United States Patent
Bagga et al.

(10) Patent No.: US 9,259,257 B2
(45) Date of Patent: Feb. 16, 2016

(54) INSTRUMENTS FOR TARGETING A JOINT DEFECT

(75) Inventors: Charanpreet S. Bagga, Basking Ridge, NJ (US); Shaun B. Hanson, West Chester, PA (US); Steven B. Cohen, West Chester, PA (US); Charles F. Leinberry, Chester Springs, PA (US); Peter F. Sharkey, Villanova, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 50 days.

(21) Appl. No.: 12/950,230

(22) Filed: Nov. 19, 2010

(65) Prior Publication Data

US 2011/0125160 A1    May 26, 2011

Related U.S. Application Data

(60) Provisional application No. 61/263,170, filed on Nov. 20, 2009, provisional application No. 61/292,979, filed on Jan. 7, 2010.

(51) Int. Cl.
*A61B 17/56* (2006.01)
*A61B 17/88* (2006.01)
(Continued)

(52) U.S. Cl.
CPC ......... *A61B 17/8872* (2013.01); *A61B 17/1764* (2013.01); *A61B 17/17* (2013.01); *A61B 17/1742* (2013.01); *A61B 17/68* (2013.01);
(Continued)

(58) Field of Classification Search
CPC ........................ A61B 17/8872; A61B 17/1764
USPC .................................. 606/86 R, 87, 88, 96
See application file for complete search history.

(56) References Cited

U.S. PATENT DOCUMENTS

| 2,697,433 | A | * | 12/1954 | Zehnder | 606/96 |
| 3,913,187 | A | * | 10/1975 | Okuda | 24/484 |
| 3,988,783 | A |   | 11/1976 | Treace |  |

(Continued)

FOREIGN PATENT DOCUMENTS

| CN | 101048111 A | 10/2007 |
| CN | 101102724 A | 1/2008 |

(Continued)

OTHER PUBLICATIONS

"U.S. Appl. No. 12/950,061, Final Office Action mailed Jul. 15, 2013", 7 pgs.

(Continued)

*Primary Examiner* — Christian Sevilla
(74) *Attorney, Agent, or Firm* — Schwegman Lundberg & Woessner, P.A.

(57) ABSTRACT

Instruments and associated methods are disclosed for treating joints, and particularly bone tissue. One of these instruments may be a positioning instrument for controlled delivery of a device to a target site of the bone tissue being treated. The positioning instrument may comprise an alignment guide having a device portal for insertion of a device therethrough. The positioning instrument may have an indicator probe having an extended arm, and a handle portion for maneuvering the positioning instrument. Another instrument may be a device for placement through the device portal of the alignment guide and to the target site. The device may comprise an implant insertion tool, an injection catheter, a cavity creation tool such as a bone drill, for example, or the device may be an implantable device.

22 Claims, 20 Drawing Sheets

(51) Int. Cl.
 *A61B 17/17* (2006.01)
 *A61B 17/68* (2006.01)
(52) U.S. Cl.
 CPC . *A61B2017/1775* (2013.01); *A61B 2017/1778* (2013.01)

(56) References Cited

U.S. PATENT DOCUMENTS

| | | | |
|---|---|---|---|
| 4,037,592 A | | 7/1977 | Kronner |
| 4,108,165 A | * | 8/1978 | Kopp et al. ............... 600/461 |
| 4,360,012 A | * | 11/1982 | McHarrie et al. ............ 606/54 |
| 4,653,487 A | | 3/1987 | Maale |
| 4,781,182 A | * | 11/1988 | Purnell et al. ............... 606/96 |
| 4,815,454 A | | 3/1989 | Dozier, Jr. |
| 4,883,048 A | * | 11/1989 | Purnell et al. ............... 606/96 |
| 4,911,153 A | | 3/1990 | Border |
| 4,920,958 A | | 5/1990 | Walt et al. |
| 4,964,861 A | | 10/1990 | Agee et al. |
| 5,098,383 A | | 3/1992 | Hemmy et al. |
| 5,163,940 A | * | 11/1992 | Bourque ..................... 606/96 |
| 5,178,164 A | | 1/1993 | Allen |
| 5,247,934 A | | 9/1993 | Wehrli et al. |
| 5,298,254 A | | 3/1994 | Prewett et al. |
| 5,324,295 A | * | 6/1994 | Shapiro ................... 606/86 R |
| 5,342,363 A | | 8/1994 | Richelsoph |
| 5,370,646 A | | 12/1994 | Reese et al. |
| 5,439,684 A | | 8/1995 | Prewett et al. |
| 5,458,602 A | * | 10/1995 | Goble et al. ................ 606/96 |
| 5,514,137 A | | 5/1996 | Coutts |
| 5,556,429 A | | 9/1996 | Felt |
| 5,595,193 A | | 1/1997 | Walus et al. |
| 5,609,636 A | | 3/1997 | Kohrs et al. |
| 5,618,549 A | | 4/1997 | Patat et al. |
| 5,681,320 A | | 10/1997 | McGuire |
| 5,741,266 A | * | 4/1998 | Moran et al. ................ 606/96 |
| 5,743,916 A | * | 4/1998 | Greenberg et al. .......... 606/102 |
| 5,755,809 A | | 5/1998 | Cohen |
| 5,766,221 A | | 6/1998 | Benderev et al. |
| 5,827,289 A | | 10/1998 | Reiley et al. |
| 5,868,749 A | | 2/1999 | Reed |
| 5,888,220 A | | 3/1999 | Felt et al. |
| 5,891,150 A | * | 4/1999 | Chan ........................... 606/96 |
| 5,928,239 A | | 7/1999 | Mirza |
| 5,968,047 A | | 10/1999 | Reed |
| 5,968,050 A | * | 10/1999 | Torrie ......................... 606/87 |
| 5,972,015 A | | 10/1999 | Scribner et al. |
| 6,010,502 A | | 1/2000 | Bagby |
| 6,036,696 A | | 3/2000 | Lambrecht et al. |
| 6,039,742 A | | 3/2000 | Krettek et al. |
| 6,048,346 A | | 4/2000 | Reiley et al. |
| 6,066,154 A | | 5/2000 | Reiley et al. |
| 6,110,211 A | | 8/2000 | Weiss |
| 6,111,164 A | | 8/2000 | Rainey et al. |
| 6,120,511 A | | 9/2000 | Chan |
| 6,140,452 A | | 10/2000 | Felt |
| 6,143,030 A | | 11/2000 | Schroder |
| 6,162,225 A | | 12/2000 | Gertzman et al. |
| 6,214,013 B1 | | 4/2001 | Lambrecht et al. |
| 6,235,043 B1 | | 5/2001 | Reiley |
| 6,241,734 B1 | | 6/2001 | Scribner |
| 6,248,110 B1 | | 6/2001 | Reiley |
| 6,248,131 B1 | | 6/2001 | Felt et al. |
| 6,254,605 B1 | | 7/2001 | Howell |
| 6,267,770 B1 | | 7/2001 | Truwit |
| 6,270,528 B1 | | 8/2001 | Mckay |
| 6,283,942 B1 | * | 9/2001 | Staehlin et al. ............. 604/116 |
| 6,285,901 B1 | | 9/2001 | Taicher et al. |
| 6,287,313 B1 | | 9/2001 | Sasso |
| 6,294,187 B1 | | 9/2001 | Boyce et al. |
| 6,306,177 B1 | | 10/2001 | Felt |
| 6,342,056 B1 | * | 1/2002 | Mac-Thiong et al. ........ 606/96 |
| 6,358,251 B1 | | 3/2002 | Mirza |
| 6,368,322 B1 | | 4/2002 | Luks et al. |
| 6,395,007 B1 | | 5/2002 | Bhatnagar |
| 6,398,811 B1 | | 6/2002 | Mckay |
| 6,423,083 B1 | | 7/2002 | Reiley et al. |
| 6,486,232 B1 | | 11/2002 | Wise et al. |
| 6,506,192 B1 | | 1/2003 | Gertzman et al. |
| 6,506,785 B2 | | 1/2003 | Evans et al. |
| 6,520,969 B2 | | 2/2003 | Lambrecht et al. |
| 6,527,773 B1 | | 3/2003 | Lin et al. |
| 6,533,794 B2 | | 3/2003 | Chakeres |
| 6,564,083 B2 | | 5/2003 | Stevens |
| 6,607,561 B2 | | 8/2003 | Brannon |
| 6,613,054 B2 | | 9/2003 | Scribner |
| 6,645,213 B2 | | 11/2003 | Sand et al. |
| 6,663,647 B2 | | 12/2003 | Reiley et al. |
| 6,719,761 B1 | | 4/2004 | Reiley |
| 6,726,691 B2 | | 4/2004 | Osorio et al. |
| 6,730,124 B2 | | 5/2004 | Steiner |
| 6,746,451 B2 | | 6/2004 | Middleton |
| 6,767,369 B2 | | 7/2004 | Boyer, II et al. |
| 6,814,736 B2 | | 11/2004 | Reiley et al. |
| 6,827,720 B2 | | 12/2004 | Leali |
| 6,863,672 B2 | | 3/2005 | Reiley et al. |
| 6,863,899 B2 | | 3/2005 | Koblish |
| 6,869,434 B2 | | 3/2005 | Choi |
| 6,875,212 B2 | | 4/2005 | Shaolian et al. |
| 6,887,246 B2 | | 5/2005 | Bhatnagar |
| 6,899,719 B2 | | 5/2005 | Reiley et al. |
| 6,917,827 B2 | | 7/2005 | Kienzle, III |
| 6,918,916 B2 | * | 7/2005 | Gobel et al. ................ 606/96 |
| 6,923,813 B2 | | 8/2005 | Phillips |
| 6,979,341 B2 | | 12/2005 | Scribner et al. |
| 6,981,981 B2 | | 1/2006 | Reiley |
| 7,001,431 B2 | | 2/2006 | Bao et al. |
| 7,029,477 B2 | * | 4/2006 | Grimm ....................... 606/88 |
| 7,063,701 B2 | | 6/2006 | Michelson |
| 7,063,702 B2 | | 6/2006 | Michelson |
| 7,087,082 B2 | | 8/2006 | Paul et al. |
| 7,094,239 B1 | | 8/2006 | Michelson |
| 7,115,146 B2 | | 10/2006 | Boyer, II et al. |
| 7,144,414 B2 | | 12/2006 | Harvie et al. |
| 7,153,305 B2 | | 12/2006 | Johnson et al. |
| 7,153,306 B2 | | 12/2006 | Ralph et al. |
| 7,153,307 B2 | | 12/2006 | Scribner |
| 7,155,306 B2 | | 12/2006 | Haitin et al. |
| 7,160,305 B2 | | 1/2007 | Schmieding |
| 7,192,431 B2 | * | 3/2007 | Hangody et al. ............. 606/87 |
| 7,226,481 B2 | | 6/2007 | Kuslich |
| 7,241,303 B2 | | 7/2007 | Reiss et al. |
| 7,250,055 B1 | | 7/2007 | Vanderwalle |
| 7,252,671 B2 | | 8/2007 | Scribner et al. |
| 7,261,716 B2 | | 8/2007 | Strobel et al. |
| 7,261,720 B2 | | 8/2007 | Stevens |
| 7,313,430 B2 | | 12/2007 | Urquhart et al. |
| 7,399,306 B2 | | 7/2008 | Reiley et al. |
| 7,410,947 B2 | | 8/2008 | Rueger et al. |
| 7,448,264 B2 | | 11/2008 | Boyce et al. |
| 7,458,977 B2 | | 12/2008 | McGinley et al. |
| 7,468,075 B2 | | 12/2008 | Lang et al. |
| 7,476,226 B2 | | 1/2009 | Weikel et al. |
| 7,477,770 B2 | | 1/2009 | Wehrli et al. |
| 7,485,119 B2 | | 2/2009 | Thelen et al. |
| 7,488,348 B2 | | 2/2009 | Truncale et al. |
| 7,491,205 B1 | | 2/2009 | Michelson |
| 7,534,226 B2 | | 5/2009 | Mernoe et al. |
| 7,545,964 B2 | | 6/2009 | Lang et al. |
| 7,550,007 B2 | | 6/2009 | Malinin |
| 7,550,011 B2 | | 6/2009 | Mckay et al. |
| 7,556,295 B2 | | 7/2009 | Holzheu |
| 7,559,932 B2 | | 7/2009 | Truckai et al. |
| 7,575,578 B2 | | 8/2009 | Wetzler et al. |
| 7,594,917 B2 | * | 9/2009 | Whittaker et al. ............ 606/98 |
| 7,608,097 B2 | | 10/2009 | Kyle |
| 7,608,098 B1 | | 10/2009 | Stone |
| 7,643,664 B2 | | 1/2010 | Wehrli et al. |
| 7,682,378 B2 | | 3/2010 | Truckai et al. |
| 7,704,256 B2 | | 4/2010 | Sand et al. |
| 7,708,742 B2 | | 5/2010 | Scribner |
| 7,713,273 B2 | | 5/2010 | Krueer et al. |
| 7,731,720 B2 | | 6/2010 | Sand et al. |
| 7,753,963 B2 | | 7/2010 | Boyer, II et al. |

(56) References Cited

U.S. PATENT DOCUMENTS

| | | | |
|---|---|---|---|
| 7,769,213 B2 | 8/2010 | Gregory et al. | |
| 7,771,431 B2 | 8/2010 | Scribner | |
| 7,789,912 B2 | 9/2010 | Manzi et al. | |
| 7,811,290 B2 | 10/2010 | Rabiner | |
| 7,837,733 B2 | 11/2010 | Collins et al. | |
| 7,837,740 B2 | 11/2010 | Semler et al. | |
| 7,840,247 B2 | 11/2010 | Liew et al. | |
| 7,846,206 B2 | 12/2010 | Oglaza et al. | |
| 7,879,038 B2 | 2/2011 | Reiley et al. | |
| 7,879,099 B2 | 2/2011 | Zipnick | |
| 7,887,543 B2 | 2/2011 | Sand et al. | |
| 7,887,546 B2 | 2/2011 | Gil et al. | |
| 7,896,885 B2 | 3/2011 | Miniaci et al. | |
| 7,901,408 B2 | 3/2011 | Ek | |
| 7,901,457 B2 | 3/2011 | Truncale et al. | |
| 7,905,924 B2* | 3/2011 | White | 623/18.11 |
| 7,914,539 B2 | 3/2011 | Stone et al. | |
| 7,927,339 B2 | 4/2011 | Ralph et al. | |
| 7,931,840 B2 | 4/2011 | Michelson | |
| 7,938,835 B2 | 5/2011 | Boucher et al. | |
| 7,959,638 B2 | 6/2011 | Osorio et al. | |
| 7,985,231 B2 | 7/2011 | Sankaran | |
| 8,029,511 B2 | 10/2011 | Bowman et al. | |
| 8,062,364 B1* | 11/2011 | Sharkey et al. | 623/16.11 |
| 8,070,753 B2 | 12/2011 | Truckai et al. | |
| 8,092,480 B2 | 1/2012 | Layne | |
| 8,133,226 B2 | 3/2012 | Chou et al. | |
| 8,142,462 B2 | 3/2012 | Middleton | |
| 8,152,813 B2 | 4/2012 | Osorio | |
| 8,168,692 B2 | 5/2012 | Wenz | |
| 8,187,327 B2 | 5/2012 | Edidin et al. | |
| 8,246,681 B2 | 8/2012 | Osorio et al. | |
| 8,608,802 B2 | 12/2013 | Bagga et al. | |
| 8,617,166 B2 | 12/2013 | Hanson et al. | |
| 8,617,176 B2* | 12/2013 | Lizardi et al. | 606/98 |
| 8,636,745 B2* | 1/2014 | Almutairi et al. | 606/96 |
| 8,801,800 B2* | 8/2014 | Bagga et al. | 623/23.48 |
| 8,821,504 B2* | 9/2014 | Sharkey et al. | 606/92 |
| 8,864,768 B2* | 10/2014 | Hanson et al. | 606/88 |
| 8,906,032 B2* | 12/2014 | Hanson et al. | 606/96 |
| 8,951,261 B2* | 2/2015 | Sharkey et al. | 606/92 |
| 9,033,987 B2 | 5/2015 | Hanson et al. | |
| 2002/0029084 A1 | 3/2002 | Paul et al. | |
| 2002/0151897 A1* | 10/2002 | Zirkle, Jr. | 606/62 |
| 2003/0009235 A1 | 1/2003 | Manrique et al. | |
| 2003/0097135 A1 | 5/2003 | Penenberg | |
| 2003/0105468 A1 | 6/2003 | Gorek | |
| 2003/0138473 A1 | 7/2003 | Koblish | |
| 2003/0220651 A1* | 11/2003 | Pusnik et al. | 606/98 |
| 2003/0225456 A1 | 12/2003 | Ek | |
| 2004/0002759 A1 | 1/2004 | Ferree | |
| 2004/0010261 A1 | 1/2004 | Hoag et al. | |
| 2004/0106925 A1 | 6/2004 | Culbert | |
| 2004/0127987 A1 | 7/2004 | Evans et al. | |
| 2004/0167538 A1 | 8/2004 | Gerber et al. | |
| 2005/0075641 A1 | 4/2005 | Singhatat et al. | |
| 2005/0119219 A1 | 6/2005 | Bellini | |
| 2005/0119753 A1 | 6/2005 | Mcgahan et al. | |
| 2005/0149022 A1 | 7/2005 | Shaolian et al. | |
| 2005/0159812 A1 | 7/2005 | Dinger, III et al. | |
| 2005/0177171 A1* | 8/2005 | Wetzler et al. | 606/96 |
| 2005/0182418 A1 | 8/2005 | Boyd et al. | |
| 2005/0203622 A1 | 9/2005 | Steiner et al. | |
| 2005/0203623 A1 | 9/2005 | Steiner et al. | |
| 2005/0256527 A1 | 11/2005 | Delfosse et al. | |
| 2005/0267584 A1 | 12/2005 | Burdulis, Jr. et al. | |
| 2005/0288795 A1 | 12/2005 | Bagga et al. | |
| 2006/0052791 A1 | 3/2006 | Hagen et al. | |
| 2006/0064164 A1 | 3/2006 | Theien | |
| 2006/0084986 A1 | 4/2006 | Grinberg et al. | |
| 2006/0247642 A1 | 11/2006 | Stone et al. | |
| 2006/0271059 A1* | 11/2006 | Reay-Young et al. | 606/96 |
| 2007/0055280 A1 | 3/2007 | Osorio et al. | |
| 2007/0100462 A1 | 5/2007 | Lang et al. | |
| 2007/0127987 A1 | 6/2007 | Altenbuchner | |
| 2007/0276370 A1 | 11/2007 | Altarac et al. | |
| 2007/0282346 A1 | 12/2007 | Scribner et al. | |
| 2008/0027434 A1 | 1/2008 | Zucherman et al. | |
| 2008/0039857 A1* | 2/2008 | Giersch et al. | 606/96 |
| 2008/0039866 A1 | 2/2008 | Stetz et al. | |
| 2008/0103506 A1* | 5/2008 | Volpi et al. | 606/96 |
| 2008/0195115 A1 | 8/2008 | Oren et al. | |
| 2008/0243127 A1 | 10/2008 | Lang et al. | |
| 2008/0281331 A1* | 11/2008 | Fritzinger et al. | 606/96 |
| 2008/0288006 A1 | 11/2008 | Brannon | |
| 2008/0306490 A1 | 12/2008 | Lakin et al. | |
| 2009/0062797 A1* | 3/2009 | Huebner et al. | 606/62 |
| 2009/0069901 A1 | 3/2009 | Truncale et al. | |
| 2009/0093813 A1* | 4/2009 | Elghazaly | 606/62 |
| 2009/0204158 A1* | 8/2009 | Sweeney | 606/309 |
| 2010/0015202 A1 | 1/2010 | Semler et al. | |
| 2010/0076503 A1 | 3/2010 | Beyar | |
| 2010/0145451 A1* | 6/2010 | Dee | 623/14.12 |
| 2010/0160970 A1 | 6/2010 | Sevrain | |
| 2010/0179549 A1 | 7/2010 | Keller | |
| 2010/0274254 A1* | 10/2010 | Boileau et al. | 606/93 |
| 2011/0125156 A1 | 5/2011 | Sharkey et al. | |
| 2011/0125157 A1* | 5/2011 | Sharkey et al. | 606/92 |
| 2011/0125159 A1 | 5/2011 | Hanson et al. | |
| 2011/0125200 A1* | 5/2011 | Hanson et al. | 606/86 R |
| 2011/0125201 A1* | 5/2011 | Hanson et al. | 606/86 R |
| 2011/0125264 A1 | 5/2011 | Bagga et al. | |
| 2011/0125265 A1 | 5/2011 | Bagga et al. | |
| 2011/0125272 A1 | 5/2011 | Bagga et al. | |
| 2014/0107781 A1 | 4/2014 | Bagga et al. | |
| 2014/0114369 A1 | 4/2014 | Hanson et al. | |
| 2014/0350683 A1* | 11/2014 | Sharkey et al. | 623/18.11 |
| 2014/0350685 A1* | 11/2014 | Bagga et al. | 623/20.16 |
| 2015/0025589 A1* | 1/2015 | Hanson et al. | 606/86 R |

FOREIGN PATENT DOCUMENTS

| | | |
|---|---|---|
| CN | 101460105 A | 6/2009 |
| CN | 102770067 A | 11/2012 |
| CN | 102781348 A | 11/2012 |
| EP | 2501303 A1 | 9/2012 |
| EP | 2501306 A1 | 9/2012 |
| EP | 2501314 A1 | 9/2012 |
| EP | 2501342 A1 | 9/2012 |
| WO | WO-03084412 A1 | 10/2003 |
| WO | WO-2005079881 A1 | 9/2005 |
| WO | WO-2008155772 A1 | 12/2008 |
| WO | WO-2011063240 A1 | 5/2011 |
| WO | WO-2011063250 A1 | 5/2011 |
| WO | WO-2011063257 A1 | 5/2011 |
| WO | WO-2011063267 A1 | 5/2011 |
| WO | WO-2011063279 A1 | 5/2011 |
| WO | WO-2011063281 A1 | 5/2011 |

OTHER PUBLICATIONS

"U.S. Appl. No. 12/950,061, Non Final Office Action mailed Feb. 7, 2013", 7 pgs.

"U.S. Appl. No. 12/950,061, Notice of Allowance mailed Oct. 1, 2013", 6 pgs.

"U.S. Appl. No. 12/950,061, Preliminary Amendment filed Feb. 8, 2011", 3 pgs.

"U.S. Appl. No. 12/950,061, Response filed Jun. 7, 2013 to Non Final Office Action mailed Feb. 7, 2013", 14 pgs.

"U.S. Appl. No. 12/950,061, Response filed Sep. 16, 2013 to Final Office Action mailed Jul. 15, 2013", 13 pgs.

"U.S. Appl. No. 12/950,097, Final Office Action mailed Dec. 10, 2013", 6 pgs.

"U.S. Appl. No. 12/950,097, Non Final Office Action mailed Feb. 15, 2013", 8 pgs.

"U.S. Appl. No. 12/950,097, Non Final Office Action mailed Aug. 6, 2013", 6 pgs.

"U.S. Appl. No. 12/950,097, Notice of Allowance mailed Apr. 2, 2014", 5 pgs.

"U.S. Appl. No. 12/950,097, Preliminary Amendment filed Feb. 7, 2011", 3 pgs.

"U.S. Appl. No. 12/950,097, Response filed Jun. 17, 2013 to Non Final Office Action mailed Feb. 15, 2013", 15 pgs.

(56) References Cited

OTHER PUBLICATIONS

"U.S. Appl. No. 12/950,097, Response filed Nov. 6, 2013 to Non Final Office Action mailed Aug. 6, 2013", 14 pgs.

"U.S. Appl. No. 12/950,097, Response filed Mar. 10, 2014 to Final Office Action mailed Dec. 10, 2013", 13 pgs.

"U.S. Appl. No. 12/950,114, Final Office Action mailed Jul. 15, 2013", 6 pgs.

"U.S. Appl. No. 12/950,114, Non Final Office Action mailed Feb. 6, 2014", 6 pgs.

"U.S. Appl. No. 12/950,114, Non Final Office Action mailed Mar. 7, 2013", 6 pgs.

"U.S. Appl. No. 12/950,114, Preliminary Amendment filed Feb. 8, 2011", 3 pgs.

"U.S. Appl. No. 12/950,114, Response filed Jun. 7, 2013 to Non Final Office Action mailed Mar. 7, 2013", 8 pgs.

"U.S. Appl. No. 12/950,114, Response filed Sep. 16, 2013 to Final Office Action mailed Jul. 15, 2013", 8 pgs.

"U.S. Appl. No. 12/950,114, Response filed May 6, 2014 to Non-Final Office Action dated Feb. 6, 2014", 7 pgs.

"U.S. Appl. No. 12/950,154, Final Office Action mailed Aug. 8, 2013", 7 pgs.

"U.S. Appl. No. 12/950,154, Non Final Office Action mailed Feb. 25, 2014", 6 pgs.

"U.S. Appl. No. 12/950,154, Non Final Office Action mailed Mar. 15, 2013", 8 pgs.

"U.S. Appl. No. 12/950,154, Preliminary Amendment filed Feb. 7, 2011", 4 pgs.

"U.S. Appl. No. 12/950,154, Response filed Jun. 17, 2013 to Non Final Office Action mailed Mar. 15, 2013", 15 pgs.

"U.S. Appl. No. 12/950,154, Response filed Oct. 8, 2013 to Final Office Action mailed Aug. 8, 2013", 18 pgs.

"U.S. Appl. No. 12/950,183, Examiner Interview Summary mailed Feb. 13, 2014", 3 pgs.

"U.S. Appl. No. 12/950,183, Final Office Action mailed Oct. 30, 2012", 16 pgs.

"U.S. Appl. No. 12/950,183, Non Final Office Action mailed May 29, 2012", 10 pgs.

"U.S. Appl. No. 12/950,183, Non Final Office Action mailed Oct. 11, 2013", 12 pgs.

"U.S. Appl. No. 12/950,183, Notice of Allowance mailed Feb. 19, 2014", 5 pgs.

"U.S. Appl. No. 12/950,183, Preliminary Amendment filed Feb. 8, 2011", 4 pgs.

"U.S. Appl. No. 12/950,183, Response filed Jan. 13, 2014 to Non Final Office Action mailed Oct. 11, 2013", 11 pgs.

"U.S. Appl. No. 12/950,183, Response filed Apr. 30, 2013 to Final Office Action mailed Oct. 30, 2012", 11 pgs.

"U.S. Appl. No. 12/950,183, Response filed May 11, 2012 to Restriction Requirement mailed Apr. 13, 2012", 2 pgs.

"U.S. Appl. No. 12/950,183, Response filed Aug. 28, 2012 to Non Final Office Action mailed May 29, 2012", 10 pgs.

"U.S. Appl. No. 12/950,183, Restriction Requirement mailed Apr. 13, 2012", 8 pgs.

"U.S. Appl. No. 12/950,183, Supplemental Amendment filed Feb. 7, 2014", 8 pgs.

"U.S. Appl. No. 12/950,273, Final Office Action mailed Nov. 6, 2012", 9 pgs.

"U.S. Appl. No. 12/950,273, Non Final Office Action mailed Apr. 13, 2012", 15 pgs.

"U.S. Appl. No. 12/950,273, Non Final Office Action mailed Apr. 25, 2014", 12 pgs.

"U.S. Appl. No. 12/950,273, Preliminary Amendment filed Feb. 8, 2011", 3 pgs.

"U.S. Appl. No. 12/950,273, Response filed Mar. 6, 2013 to Final Office Action mailed Nov. 6, 2012", 10 pgs.

"U.S. Appl. No. 12/950,273, Response filed Jul. 12, 2012 to Non Final Office Action mailed Apr. 13, 2012", 12 pgs.

"U.S. Appl. No. 12/950,306, Final Office Action mailed Nov. 26, 2012", 9 pgs.

"U.S. Appl. No. 12/950,306, Non Final Office Action mailed Jun. 14, 2012", 11 pgs.

"U.S. Appl. No. 12/950,306, Notice of Allowance mailed May 28, 2013", 9 pgs.

"U.S. Appl. No. 12/950,306, Notice of Allowance mailed Aug. 13, 2013", 9 pgs.

"U.S. Appl. No. 12/950,306, Preliminary Amendment filed Feb. 8, 2011", 7 pgs.

"U.S. Appl. No. 12/950,306, Response filed Apr. 30, 2013 to Final Office Action mailed Nov. 26, 2012", 15 pgs.

"U.S. Appl. No. 12/950,306, Response filed Sep. 13, 2012 to Non Final Office Action mailed Jun. 14, 2012", 11 pgs.

"U.S. Appl. No. 12/950,355, Final Office Action mailed Mar. 12, 2013", 15 pgs.

"U.S. Appl. No. 12/950,355, Non Final Office Action mailed Aug. 13, 2012", 16 pgs.

"U.S. Appl. No. 12/950,355, Response filed Jan. 14, 2013 to Non Final Office Action mailed Aug. 13, 2012", 17 pgs.

"U.S. Appl. No. 12/950,355, Response filed Jul. 12, 2013 to Final Office Action mailed Mar. 12, 2013", 20 pgs.

"Chinese Application Serial No. 201080052578.1, Office Action mailed Apr. 1, 2014", w/English Translation, 11 pgs.

"Chinese Application Serial No. 201080052580.9, Office Action mailed Apr. 3, 2014", w/English Translation, 13 pgs.

"Chinese Application Serial No. 201080052583.2, Office Action mailed Mar. 14, 2014", w/English Translation, 9 pgs.

"European Application Serial No. 10832277.7, Office Action mailed Jun. 27, 2012", 2 pgs.

"European Application Serial No. 10832285.0, Office Action mailed Jun. 27, 2012", 2 pgs.

"International Application Serial No. Jan. 24, 2011, International Preliminary Report on Patentability mailed May 22, 2012", 9 pgs.

"International Application Serial No. PCT/US2010/057426, International Search Report and Written Opinion mailed Jan. 24, 2011", 10 pgs.

"International Application Serial No. PCT/US2010/057440, International Preliminary Report on Patentability mailed May 22, 2012", 7 pgs.

"International Application Serial No. PCT/US2010/057440, International Search Report and Written Opinion mailed Feb. 7, 2011", 8 pgs.

"International Application Serial No. PCT/US2010/057456, International Preliminary Report on Patentability mailed May 22, 2012", 6 pgs.

"International Application Serial No. PCT/US2010/057456, International Search Report and Written Opinion mailed Jan. 14, 2011", 7 pgs.

"International Application Serial No. PCT/US2010/057471, International Preliminary Report on Patentability mailed May 31, 2012", 7 pgs.

"International Application Serial No. PCT/US2010/057471, International Search Report mailed Jan. 18, 2011", 2 pgs.

"International Application Serial No. PCT/US2010/057471, Written Opinion mailed Jan. 18, 2011", 5 pgs.

"International Application Serial No. PCT/US2010/057475, International Preliminary Report on Patentability mailed May 22, 2012", 6 pgs.

"International Application Serial No. PCT/US2010/057475, International Search Report mailed Jan. 18, 2011", 8 pgs.

"International Application Serial No. PCT/US2010/057475, Written Opinion mailed Jan. 18, 2011", 5 pgs.

"International Application Serial No. PCT/US2010/057483, International Preliminary Report on Patentability mailed May 22, 2012", 6 pgs.

"International Application Serial No. PCT/US2010/057483, International Search Report and Written Opinion mailed Feb. 2, 2011", 7 pgs.

"International Application Serial No. PCT/US2010/057498, International Preliminary Report on Patentability mailed May 22, 2012", 5 pgs.

"International Application Serial No. PCT/US2010/057498, International Search Report mailed Jan. 24, 2011", 2 pgs.

(56) References Cited

OTHER PUBLICATIONS

"International Application Serial No. PCT/US2010/057498, Written Opinion mailed Jan. 24, 2011", 4 pgs.
"International Application Serial No. PCT/US2010/057500, International Preliminary Report on Patentability mailed May 31, 2012", 8 pgs.
"International Application Serial No. PCT/US2010/057500, International Search Report mailed Jan. 27, 2011", 2 pgs.
"International Application Serial No. PCT/US2010/057500, Written Opinion mailed Jan. 27, 2011", 6 pgs.
May 12, 2008 Riddle Memorial Hospital, Medial, PA 19063 Operative Report. Surgeon: Peter F Sharkey, M.D.; Right knee, medial tibial plateau; A cannulated bone biopsy needle was placed into the bone under fluoroscopic guidance; Implant used: Stryker Orthopedics Hydroset (Bone Substitute Material); Surgeon also expressed difficulty in injecting the bone substitute.
Oct. 27, 2008 SPU Operative Report. Surgeon: Steven B Cohen, M.D.; An Anterior Cruciate Ligament (ACL) portal-creation device was repurposed for this surgery; The tibial probe was placed on the medial femoral condyle, with the tunnel guide secured proximally on the thigh; The surgeon expressed difficulty in positioning and stabilizing the guide; A cannulated pin was placed through the tunnel guide and placed distally into the medial femoral condyle; No implant was injected into the bone.
Nov. 10, 2008 SPU Operative Report. Surgeon: Steven B Cohen, M.D.; Treatment of the central medial tibial plateau; A guide pin was inserted into the medial tibial plateau; An endo button drill bit was used to expand the drill hole; One cubic centimeter (cc) of cement was inserted into the bone; A second drill hole was made from below, and a second cc was inserted into the bone.
"U.S. Appl. No. 12/950,273, Final Office Action mailed Feb. 4, 2015", 28 pgs.
"U.S. Appl. No. 14/109,368, Non Final Office Action mailed Mar. 11, 2015", 6 pgs.
"U.S. Appl. No. 14/143,883, Notice of Allowance mailed Jan. 26, 2015", 6 pgs.
"U.S. Appl. No. 14/454,298, Notice of Allowance mailed Mar. 17, 2015", 8 pgs.
"U.S. Appl. No. 14/508,436, Preliminary Amendment filed Jan. 8, 2015", 7 pgs.
"U.S. Appl. No. 14/617,058, Preliminary Amendment filed Feb. 18, 2015", 8 pgs.
"Chinese Application Serial No. 201080052569.2 Response filed Nov. 7, 2014 to Non Final Office Action mailed Jun. 10, 2014", (W/ English Translation), 12 pgs.
"Chinese Application Serial No. 201080052569.2, Office Action mailed Jan. 28, 2015", (W/ English Translation), 5 pgs.
"Chinese Application Serial No. 201080052578.1, Office Action mailed Dec. 17, 2014", (W/ English Translation), 4 pgs.
"Chinese Application Serial No. 201080052578.1, Response filed Jan. 22, 2015 to Office Action mailed Dec. 17, 2014", (W/ English Translation), 8 pgs.
"Chinese Application Serial No. 201080052583.2, Office Action mailed Dec. 24, 2014", (W/ English Translation), 4 pgs.
"Chinese Application Serial No. 201080052583.2, Response filed Sep. 26, 2014 to Office Action mailed Mar. 14, 2014", (W/ English Translation of Claims), 10 pgs.
"U.S. Appl. No. 14/109,368, Final Office Action mailed Jul. 9, 2015", 10 pgs.
"U.S. Appl. No. 14/454,298, Notice of Allowance mailed Jul. 1, 2015", 6 pgs.
"U.S. Appl. No. 14/724,160, Preliminary Amendment filed Jun. 17, 2015", 8 pgs.
"U.S. Appl. No. 12/950,273, Advisory Action mailed May 12, 2015", 3 pgs.
"U.S. Appl. No. 12/950,273, Response filed May 4, 2015 to Final Office Action mailed Feb. 4, 2015", 14 pgs.
"U.S. Appl. No. 12/950,273, Response filed Jun. 4, 2015 to Final Office Action mailed Feb. 4, 2015", 14 pgs.
"U.S. Appl. No. 14/109,368, Response filed May 26, 2015 to Non-Final Office Action mailed Mar. 11, 2015", 12 pgs.
"U.S. Appl. No. 14/695,516, Preliminary Amendment filed May 27, 2015", 6 pgs.
"Australian Application Serial No. 2010321745, Office Action mailed Jan. 12, 2015", 3 pgs.
"Australian Application Serial No. 2010321745, Response filed Apr. 24, 2015 to Office Action mailed Jan. 12, 2015", (18 pgs).
"Australian Application Serial No. 2010321812, Office Action mailed Jan. 12, 2015", 3 pgs.
"Australian Application Serial No. 2010321812, Response filed Apr. 24, 2015 to Office Action mailed Jan. 12, 2015", 19 pgs.
"Chinese Application Serial No. 201080052569.2, Response filed Mar. 26, 2015 to Office Action mailed Jan. 28, 2015", W/ English Claims, 10 pgs.
"Chinese Application Serial No. 201080052578.1, Response filed Aug. 12, 2014 to Office Action mailed Apr. 1, 2014", W/ English Claims, 13 pgs.
"Chinese Application Serial No. 201080052580.9, Response filed Aug. 14, 2014 to Office Action mailed Apr. 3, 2014", W/ English Claims, 12 pgs.
"U.S. Appl. No. 12/950,355, Notice of Allowance mailed Dec. 9, 2014", 6 pgs.
"U.S. Appl. No. 14/143,883, Response filed Dec. 4, 2014 to Non-Final Office Action mailed Aug. 4, 2014", 9 pgs.
"Chinese Application Serial No. 201080052580.9, Office Action mailed Nov. 25, 2014", (W/ English Translation), 18 pgs.
"U.S. Appl. No. 12/950,097, Notice of Allowance mailed Jul. 9, 2014", 5 pgs.
"U.S. Appl. No. 12/950,114, Notice of Allowance mailed Jun. 16, 2014", 5 pgs.
"U.S. Appl. No. 12/950,154, Examiner Interview Summary mailed Aug. 19, 2014", 3 pgs.
"U.S. Appl. No. 12/950,154, Notice of Allowance mailed Oct. 10, 2014", 6 pgs.
"U.S. Appl. No. 12/950,154, Response filed Aug. 25, 2014 to Non-Final Office Action mailed Feb. 25, 2014", 18 pgs.
"U.S. Appl. No. 12/950,183, Notice of Allowance mailed Jun. 6, 2014", 7 pgs.
"U.S. Appl. No. 12/950,273, Response filed Oct. 24, 2014 to Non-Final Office Action mailed Apr. 25, 2014", 14 pgs.
"U.S. Appl. No. 12/950,355, Non Final Office Action mailed Jul. 29, 2014", 9 pgs.
"U.S. Appl. No. 12/950,355, Response filed Oct. 28, 2014 to Non-Final Office Action dated Jul. 29, 2014", 21 pgs.
"U.S. Appl. No. 14/143,883, Non Final Office Action mailed Aug. 4, 2014", 6 pgs.
"U.S. Appl. No. 14/453,301, Preliminary Amendment filed Oct. 6, 2014", 8 pgs.
"U.S. Appl. No. 14/454,298, Preliminary Amendment filed Sep. 18, 2014", 7 pgs.
"Chinese Application Serial No. 201080052569.2, Office Action mailed Apr. 25, 2014", w/English Translation, 17 pgs.

* cited by examiner

INSTRUMENTS FOR TARGETING A JOINT DEFECT

CROSS-REFERENCE TO RELATED APPLICATIONS

This application claims priority to U.S. Provisional No. 61/292,979 filed Jan. 7, 2010, and entitled "INSTRUMENTS AND IMPLANTS FOR JOINT REPAIR AND METHODS OF USE," and U.S. Provisional No. 61/263,170 filed Nov. 20, 2009, and entitled "METHOD FOR TREATING JOINT PAIN AND ASSOCIATED INSTRUMENTS," which are herein incorporated by reference in their entirety.

This application also relates to and co-owned U.S. patent application Ser. No. 12/950,355, filed Nov. 19, 2010 and entitled "SUBCHONDRAL TREATMENT OF JOINT PAIN," the content of which is herein incorporated in its entirety by reference.

FIELD

The present invention relates to devices and tools for surgical treatment of joints, and more particularly to instruments, implants and associated methods for the surgical repair and treatment of bone tissue at these joints.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support. Injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

One of the difficulties of currently available surgical access devices and insertion tools is the ability to target a specific area of the bone to be treated, in a fast, accurate and easy manner. Currently available surgical insertion tools require the surgeon to take multiple steps with multiple instruments in order to access, locate, and treat the target defect site. This results in additional and unnecessary time in the operating room, as well as risks for complications since numerous instruments and maneuvers are at play.

Accordingly, it is desirable to provide instruments that allow fast, easy and precise surgical access to the target site, or the bone defect, to be treated. It is further desirable to provide implants effective for bone repair that can be used with these instruments.

SUMMARY

The present disclosure provides instruments, implants and associated methods for the surgical repair and treatment of bone tissue, particularly of bone tissue at joints. In one embodiment, a positioning instrument is provided for controlled delivery of a device to a target site of the bone tissue being treated. The positioning instrument may comprise an alignment guide having a device portal for insertion of a device therethrough. The device portal may be configured to provide accurate and controlled delivery of the device to the target site. A plurality of device portals may be provided, with each portal defining a specific distance and spatial orientation with respect to one another and also to the target site. The device portals may be keyed to the shape of the device to provide anti-rotation features. An indicator probe having an extended arm may be provided to allow the clinician to locate the target site during surgery using the indicator probe as a reference. The indicator probe may be configured for placement against an anatomical landmark of the bone.

In another embodiment, an implantable device for insertion into bone tissue may be provided. The implantable device can comprise an elongate body extending between a proximal, leading end and a distal, trailing end, the distal end including a tool-receiving portion for receiving a tool, the proximal end having a tapered tip, and be configured for enhanced bone tissue engagement. The implantable device may include a surface feature such as fins, for example. The fins may either be uniform in height along its length, or they may vary in height. The implantable device may be fenestrated, with a channel extending through the elongate body for introduction of a material such as a bone cement, for example.

In still another embodiment, an insertion tool is provided for the introduction of the implantable device to the target site. The insertion tool may comprise a gripping end, a shaft extending from the gripping end and terminating at a device-engaging end, and a depth stop to prevent overextension of the insertion tool into the bone tissue. The depth stop may be configured to be adjustable along the length of the shaft, so that the clinician may control how deep the implantable device travels into the bone tissue and to the target site.

In yet another embodiment, a system for repairing bone tissue at a joint is provided. The system may include a positioning instrument for controlled delivery of a device to a target site of the bone tissue being treated. The positioning instrument may comprise an alignment guide having a device portal for insertion of a device therethrough. The system may also include a device for placement through the device portal of the alignment guide and to the target site. The device may comprise an implant insertion tool, an injection catheter, a cavity creation tool such as a bone drill, tamp or expansion device, for example, or the device may be an implantable device.

In still yet another embodiment, a method for treating a bone defect at a joint is provided. The method may include the steps of providing a positioning instrument for controlled delivery of a device to a target site in the bone tissue, the positioning instrument comprising an alignment guide having a device portal for insertion of a device therethrough, wherein the device portal is configured to provide accurate and controlled delivery of the device to the target site, and introducing a device through the device portal of the alignment guide and to the target site. The device may comprise an implant insertion tool, an injection catheter, a cavity creation tool such as a bone drill, tamp or expansion device, for example, or the device may be an implantable device.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DESCRIPTION OF THE EMBODIMENTS

Figure 1A:
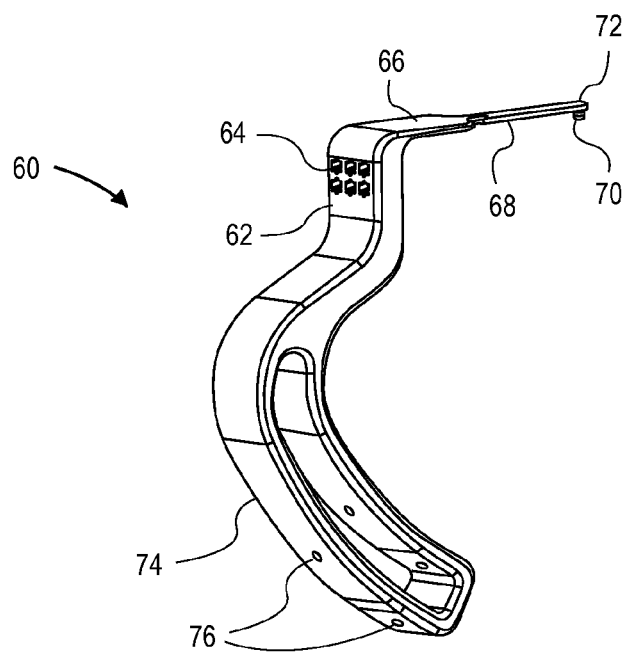
FIG. 1A illustrates an exemplary embodiment of a positioning instrument of the present invention.

The present disclosure provides a methodology, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, the embodiments diagnose and treat pain at its source in the subchondral region of a bone of a joint to relieve the pain. Applicants have discovered that pain associated with joints, especially osteoarthritic joints, can be correlated to bone defects or changes at the subchondral level rather than, for example, the severity of osteoarthritic progression or defects at the articular surface level. In particular, bone defects, such as bone marrow lesions, edema, fissures, fractures, hardened bone, etc. near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal healing function, thus leading to a resolution of the inflammation surrounding the defect.

Applicants have discovered that treatment of the bone by mechanical and biological means to restore the normal physiologic stress distribution, and restore the healing balance of the bone tissue at the subchondral level, is a more effective way of treating pain than conventional techniques. That is, treatment can be effectively achieved by mechanically strengthening or stabilizing the defect, and biologically initiating or stimulating a healing response to the defect. Accordingly, the present disclosure provides methods, devices, and systems for a subchondral procedure. This procedure and its associated devices, instruments, etc. are also marketed under the registered trademark name of SUBCHONDROPLASTY™. The SUBCHONDROPLASTY™ procedure is a response to a desire for an alternative to patients facing partial or total knee replacement.

In general, the SUBCHONDROPLASTY™ or SCP™ technique is intended to both strengthen the bone and stimulate the bone. In SCP™, bone fractures or non-unions are stabilized, integrated or healed, which results in reduction of a bone defect, such as a bone marrow lesion or edema. In addition, SCP™ restores or alters the distribution of forces in a joint to thereby relieve pain. SCP™ can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY™ generally comprises evaluating a joint, for example, by taking an image of the joint, detecting the presence of one or more subchondral defects, diagnosing which of these subchondral defects is the source of pain, and determining an extent of treatment for the subchondral defect. The present technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. The present disclosure provides several exemplary treatment modalities for SCP™ for the different extents of treatment needed. Accordingly, a medical practitioner may elect to use the techniques and devices described herein to subchondrally treat any number of bone defects as he deems appropriate.

In some embodiments, detection and identification of the relevant bone marrow lesion or bone marrow edema (BML or BME) can be achieved by imaging, e.g., magnetic resonance imaging (MRI), X-ray, manual palpation, chemical or biological assay, and the like. A T1-weighted MRI can be used to detect sclerotic bone, for example. Another example is that a T2-weighted MRI can be used to detect lesions, edemas, and cysts. X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP™ treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface or periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP™ treatments can be administered on acute stress fractures, BML or BME, or other subchondral defects, as previously mentioned.

According to the embodiments, the SCP™ treatment may continue after surgery. In particular, the patient may be monitored for a change in pain scores, or positive change in function. For example, patients are also checked to see when they are able to perform full weight-bearing activity and when they can return to normal activity. Of note, if needed, the SCP™ procedure can be completely reversed in the event that a patient requires or desires a joint replacement or other type of procedure. The SCP™ treatment may also be performed in conjunction with other procedures, such as cartilage resurfacing, regeneration or replacement, if desired.

The present disclosure provides a number of treatment modalities, and associated devices, instruments and related methods of use for performing SUBCHONDROPLASTY™. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP™, the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface. In another embodiment, the injection can be made at an angle to the joint surface. In yet another embodiment, the injection can be made below a bone marrow lesion.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP™. For instance, stimulation of bone tissue in SCP™ may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implant may be placed in cancellous bone, through sclerotic bone, or under sclerotic bone at the affected bone region. The implant may also be configured as a bi-cortical bone implant. In one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the affected bone region, such as into the lower region of a bone marrow lesion or below the lesion. For example, the implant may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Accordingly, the present disclosure also provides suitable implantable fixation devices for the surgical treatment of these altered bone regions or bone defects, especially at the subchondral level. Applicants have also discovered devices and instruments that can be used in combination with cements or hardening materials commonly used to repair damaged bone by their introduction into or near the site of damage, either to create a binding agent, cellular scaffold or mechanical scaffold for immobilization, regeneration or remodeling of the bone tissue.

In general, the embodiments relate to instruments, implants and associated methods for the surgical treatment of a joint, and particularly to a bone defect at that joint region. Applicants have discovered that pain associated with osteoarthritic joints can be correlated to bone defects at the subchondral level. In particular, bone defects such as bone marrow lesions, edemas, fissures, fractures, etc. near sclerotic tissue lead to abnormal stress distribution of the joint, which causes inflammation and generates pain. By altering the makeup of the sclerotic bone in relation to the surrounding region, it is possible to change the structural integrity of the damaged bone, leading to a resolution of the inflammation. Applicants have discovered that treatment of the bone defects in an effort to alter the structural makeup of damaged sclerotic bone leads to reduced inflammation and pain. Over time, normal physiologic stress distribution can be achieved, and mechanical congruity restored, thereby resulting in healing of the damage and reduction to elimination of pain. Accordingly, the present invention provides suitable instruments, implants and associated methods for the surgical treatment of these bone defects, especially at the subchondral level near sclerotic bone.

As previously mentioned, there is a need for surgical instruments that allow fast, easy and precise surgical access to the target site, or the bone defect, to be treated. Applicants have discovered instruments are particularly suitable for accessing certain areas of the bone within the range of about 2-15 mm from the bone surface, such as the articular surface or the subchondral bone area, and therefore require more precise defect location features. These instruments are also particularly suited to aid in the insertion of tools, devices, implants, etc. in a parallel orientation with respect to the top surface of the bone to be treated. Further, it is known to repair damaged bone by introducing a material into or near the site of damage, either to create a binding agent, cellular scaffold or mechanical scaffold for immobilization, regeneration or remodeling of the bone tissue. Applicants have also discovered implants effective for bone repair that can be used in combination with these surgical instruments.

Figure 1B:
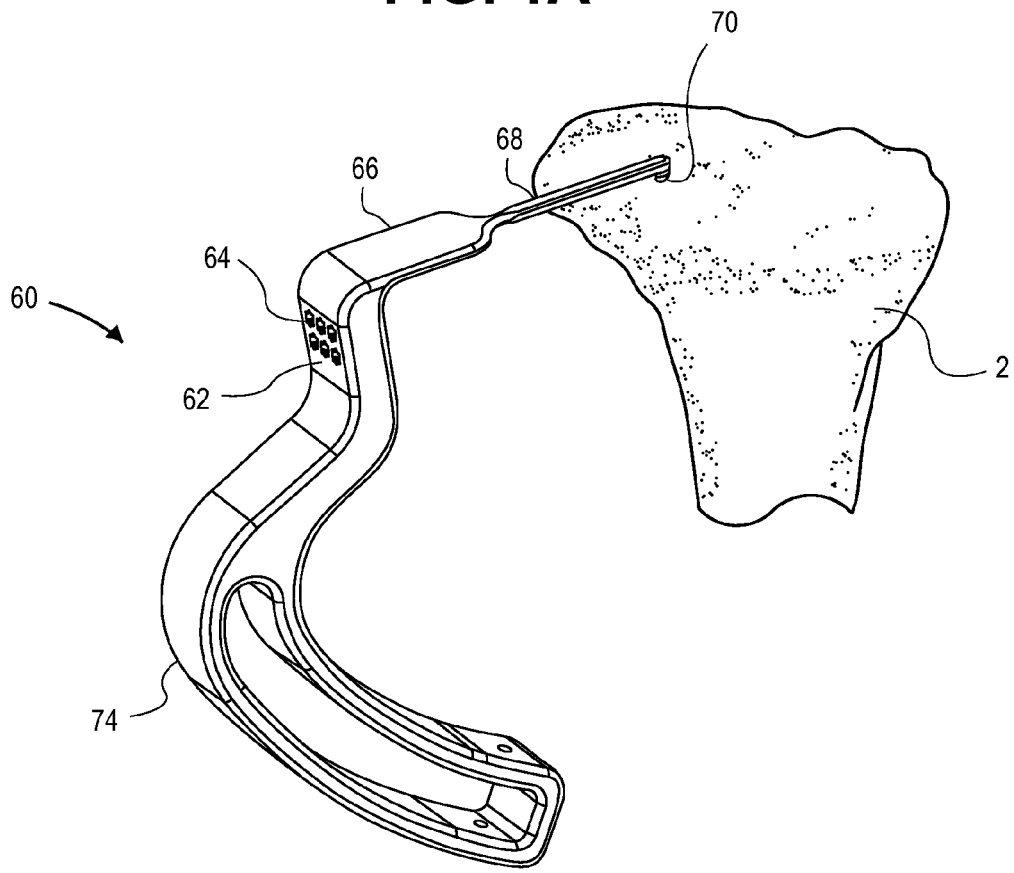
FIG. 1B illustrates the positioning instrument of FIG. 1A in situ.
Figure 2A:
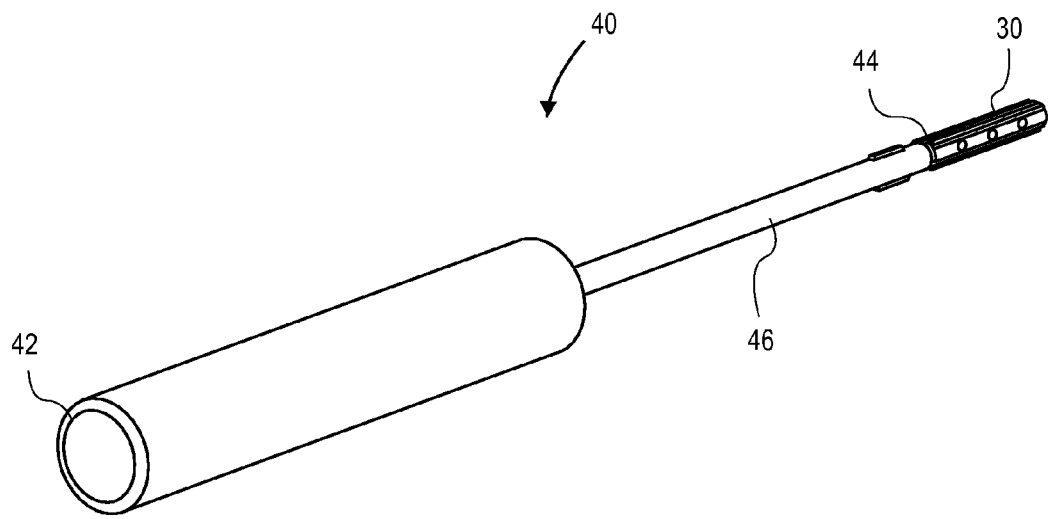
FIG. 2A illustrates a perspective view of an exemplary insertion tool with an exemplary implantable device.
Figure 3A:
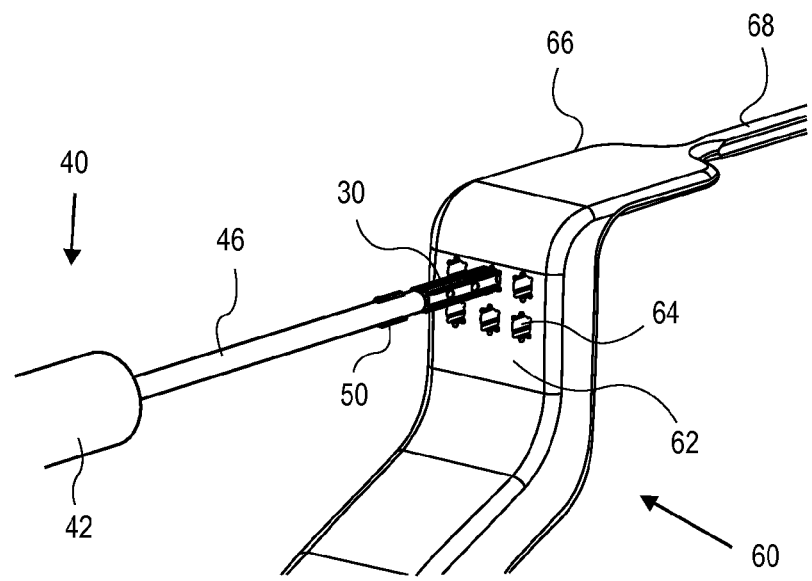
FIGS. 3A-3D illustrate various steps of using the insertion tool and implantable device of FIG. 2A with the positioning instrument of FIG. 1A.

Turning now to the drawings and in particular to FIGS. 1A and 1B, an exemplary embodiment of a positioning instrument 60 of the present disclosure. The positioning instrument 60 allows controlled delivery of a device to the target site in the bone. The term "device" is used herein to describe generally any number of implantable devices, materials and instruments suitable for bone treatment and/or repair. As will be described in more detail below, the device may be an implantable device such as implant 30 as shown in FIGS. 2A and 3A. The device may also be an insertion tool 40, a drill, an injection needle, or a catheter. Accordingly, the positioning instrument 60 may be used to provide quick, easy and accurate access to a specific target site for a number of instruments or implants that can perform any variety of treatment functions at that site.

As shown, the positioning instrument 60 can include an alignment guide 62 that serves as a jig, or a box/frame for guiding a device to a specific location on the bone being treated. One or more device portals 64 may be provided on the alignment guide 62. The positioning instrument 60 can also include an indicator probe 66 for visually identifying the target site. The indicator probe 66 can include an extended arm 68 having a suitable length to access the bone to be treated. The extended arm 68 can include a protrusion, or knob 70, at the terminal end 72 of the extended arm 68. A handle portion 74 may be provided for maneuvering the positioning instrument 60 in place during surgery. The handle portion may include holes 76 for receiving other tools such as pins for stabilizing the positioning instrument 60, as will be described in more detail below.

FIG. 2A illustrates an exemplary embodiment of an insertion tool 40 in use with an exemplary implantable fenestrated device 30. The fenestrated implantable device 30 can be of the type disclosed in U.S. patent application Ser. No. 12/950,306, filed Nov. 19, 2010 and entitled "IMPLANTABLE DEVICES FOR SUBCHONDRAL TREATMENT OF JOINT PAIN," which is hereby incorporated in its entirety by reference. Other exemplary implantable devices are disclosed in co-pending and co-owned U.S. patent application Ser. No. 12/950,273, filed Nov. 19, 2010 and entitled "IMPLANTABLE DEVICES FOR SUBCHONDRAL TREATMENT OF JOINT PAIN," and U.S. patent application Ser. No. 12/950,183, filed Nov. 19, 2010 and entitled "BONE-DERIVED IMPLANTABLE DEVICES FOR SUBCHONDRAL TREATMENT OF JOINT PAIN," the contents of which are herein incorporated in their entirety by reference.

Figure 2B:
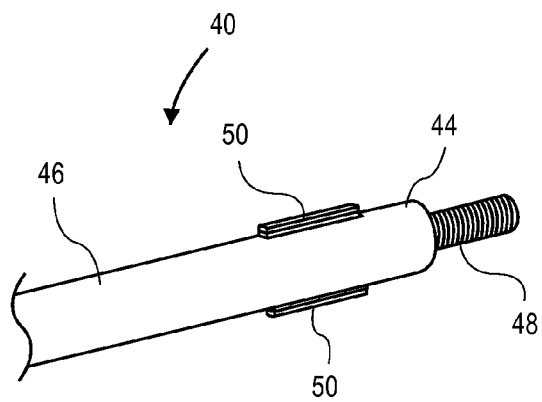
FIG. 2B illustrates an enlarged view of the tip of the insertion tool of FIG. 2A.

Insertion tool 40 may include a gripping end 42 and terminate at a device-engaging end 44. The device-engaging end 44 may further include a tip 48 that mates with the tool-engaging portion of the implant 30. As shown in FIG. 2B, the tip 48 may be threaded, and the tool-engaging portion may comprise a threaded bore, for example. However, it is understood that the tip 48 and the corresponding bore or tool-engaging portion of the implant 30 may be configured in any suitable complementary fashion as well known in the art, so long as the configuration provides adequate fit and release. For example, the tip 48 may be provided with a desired shape, while the bore may be provided with a complementary shape to receive the tip 48 in an interference fit-type fashion.

An elongate shaft 46 can extend between the gripping end 42 and the device-engaging end 44. The elongate shaft 46 may include a depth stop 50 to prevent overextension of the insertion tool 40 into bone tissue. The depth stop 50 may be stationary, or it may be adjustable along the length of the shaft 46 to allow customization of the tool 40 to the patient's anatomy. In one embodiment, a mechanism (not shown) may be provided to allow adjustment of the depth stop 50 at the gripping end 42. This mechanism may be internal to the tool 40. Alternatively, the depth stop 50 may be configured as a slidable element on the shaft 46. For instance, the shaft 46 may be provided with tracks (not shown) on which the depth stop 50 may sit. The depth stop 50 may be manually adjusted on the tracks to the desired depth needed by the clinician.

FIGS. 1B and 3A-3D illustrate various steps for using the positioning instrument 60. As shown in FIG. 1B, the positioning instrument 60 can be positioned such that the indicator probe 66 rests on the top surface of a bone 2. In the illustrated example, the bone 2 may be a tibia for a knee joint repair. It is understood, however, that the bone 2 may be any other type of bone found in a joint, such as a hip, ankle or shoulder. Knob 70 can be used to visually indicate where the bone defect resides.

Each portal 64 has a predetermined distance and spatial relationship relative to the other portals 64, such that the clinician can determine with accuracy the depth of the portal 64 relative to the indicator probe 66 and consequently the top surface of the bone 2. The portals 64 serve as spatial references or orientation or location markers for the clinician. If desired, the alignment guide 62 may include indicia to show the distance of each portal 64 below the indicator probe 66. As previously discussed, the device portals 64 are configured to provide accurate and controlled delivery of a device to the target site indicated by the indicator probe 66. The portals 64 may be configured at any desired angle relative to the alignment guide 62. In one embodiment, the portals 64 may be angularly configured to guide, or direct, the device in a parallel direction relative to the top of the bone being treated. In another embodiment, the portals 64 may be angularly configured to direct the device in a perpendicular direction relative to the top of the bone, for example. Thus, the positioning instrument 60 may be particularly suited to enable implants 30 to be inserted parallel or at an angle (i.e., acute, perpendicular, etc.) to the top bone surface in an easy, fast and precise manner.

Figure 3B:
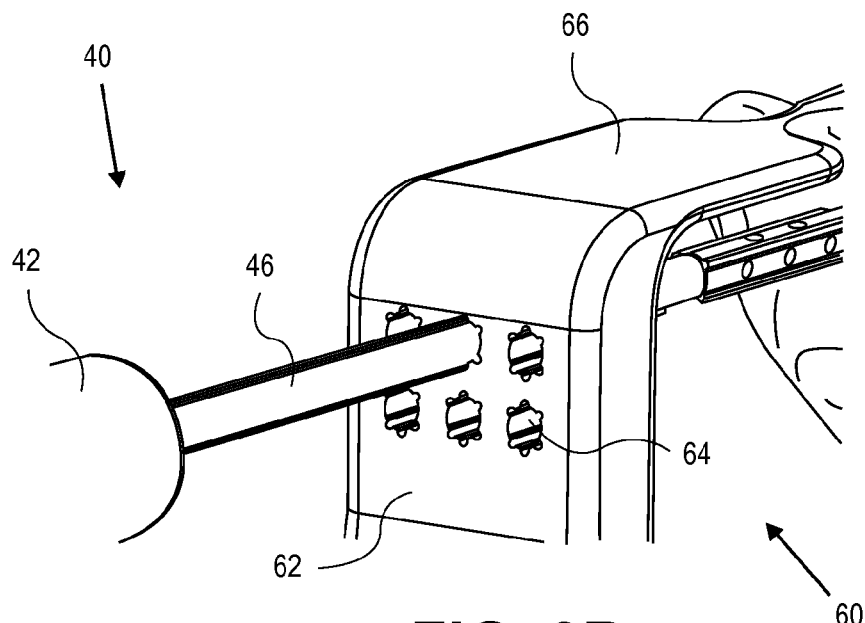
Figure 3C:
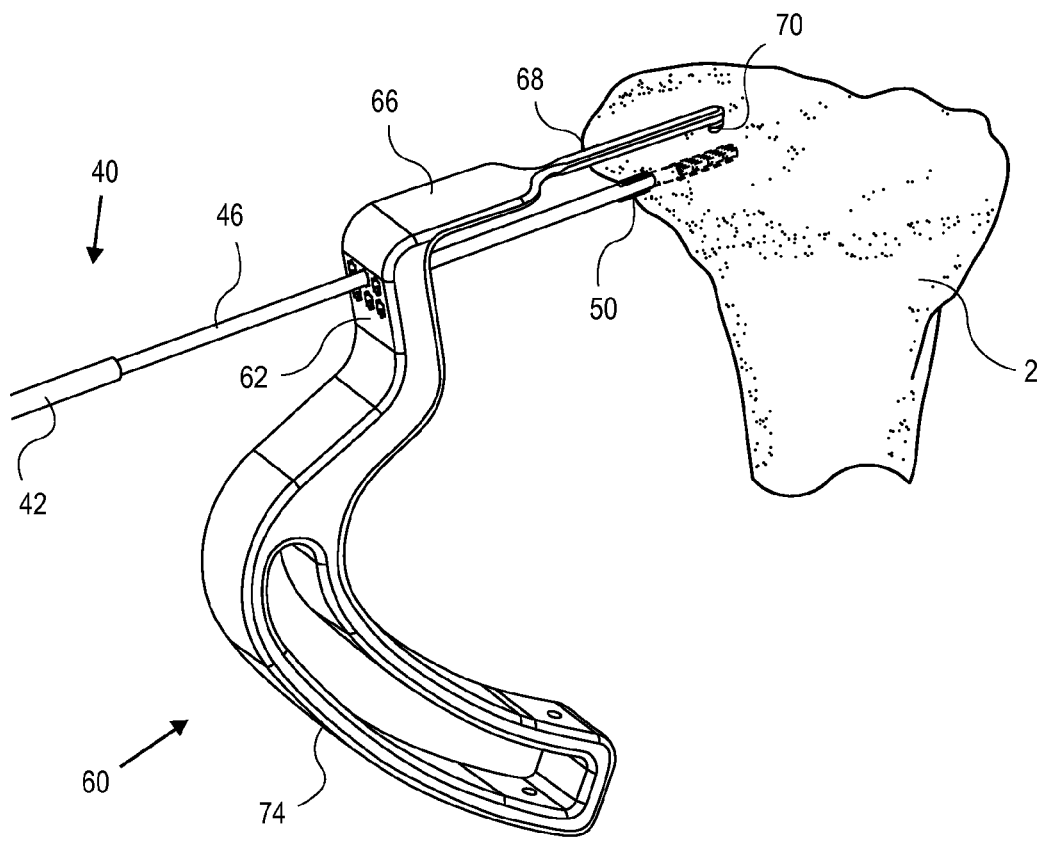
Figure 3D:
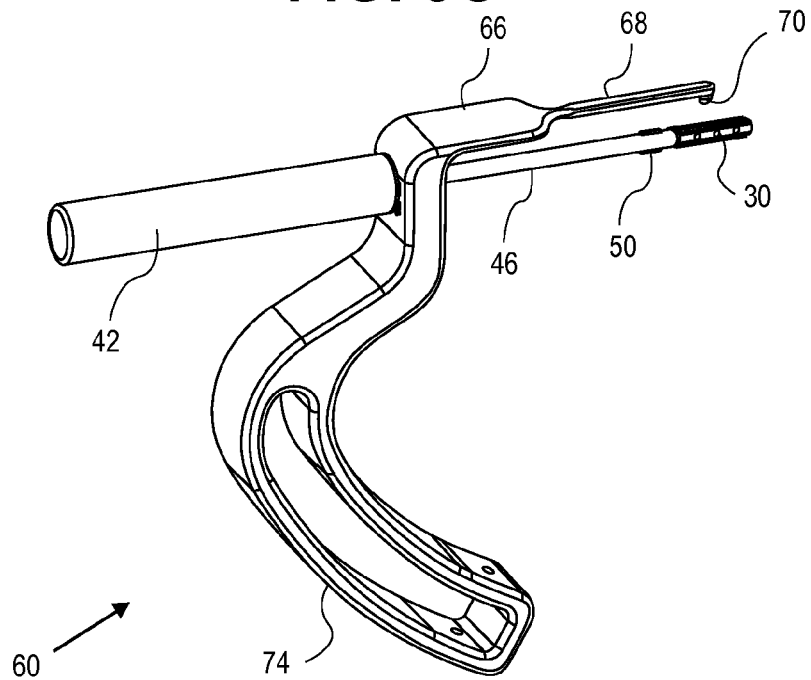

FIGS. 3A and 3B illustrate how the device portals 64 can include an anti-rotation feature. As shown, the device portals 64 may be keyed, or shaped with a specific configuration that matches with a shape configuration of the device to be inserted. In the case of implant 30, the device portals 64 may be shaped to accommodate the fins 20 of the implant 30 in a certain orientation. The keyed device portals 64 allow the implant 30 to enter, along with the shaft 46 of the insertion tool 40 and the depth stops 50 attached thereto, and to move freely in a linear direction in and out of the portals 64 as represented in FIGS. 3C and 3D. However, the keyed device portals 64 may not allow free rotation thereabout. Thus, the anti-rotation feature provides a further level of control for the clinician.

In some embodiments, the device portals can have removable collars around them to act as depth stops (not shown). It is contemplated that the collars can be of a snap on, snap off type. Additionally, it is contemplated that an exterior template (not shown) having a plurality of shaped holes corresponding to the device portals 64 may be applied onto the alignment guide 62. The template would enable the clinician to alter the shape or "key" of the portals 64 as needed. Furthermore, the template may include alternate spatial arrangements to block out certain portals while allowing access of other portals.

Figure 4A:
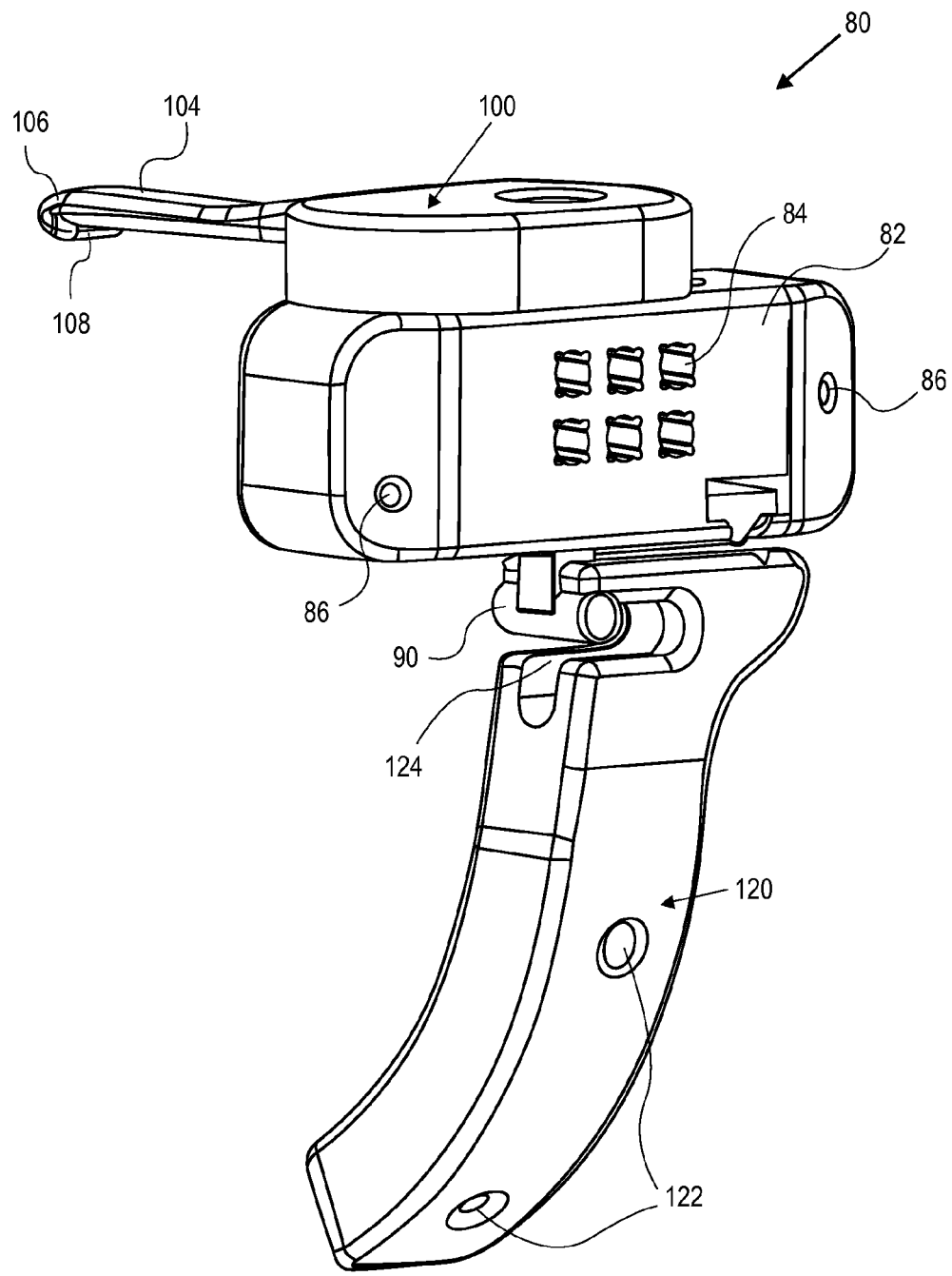
FIG. 4A illustrates a front view of another exemplary embodiment of a positioning instrument of the present invention.
Figure 4B:
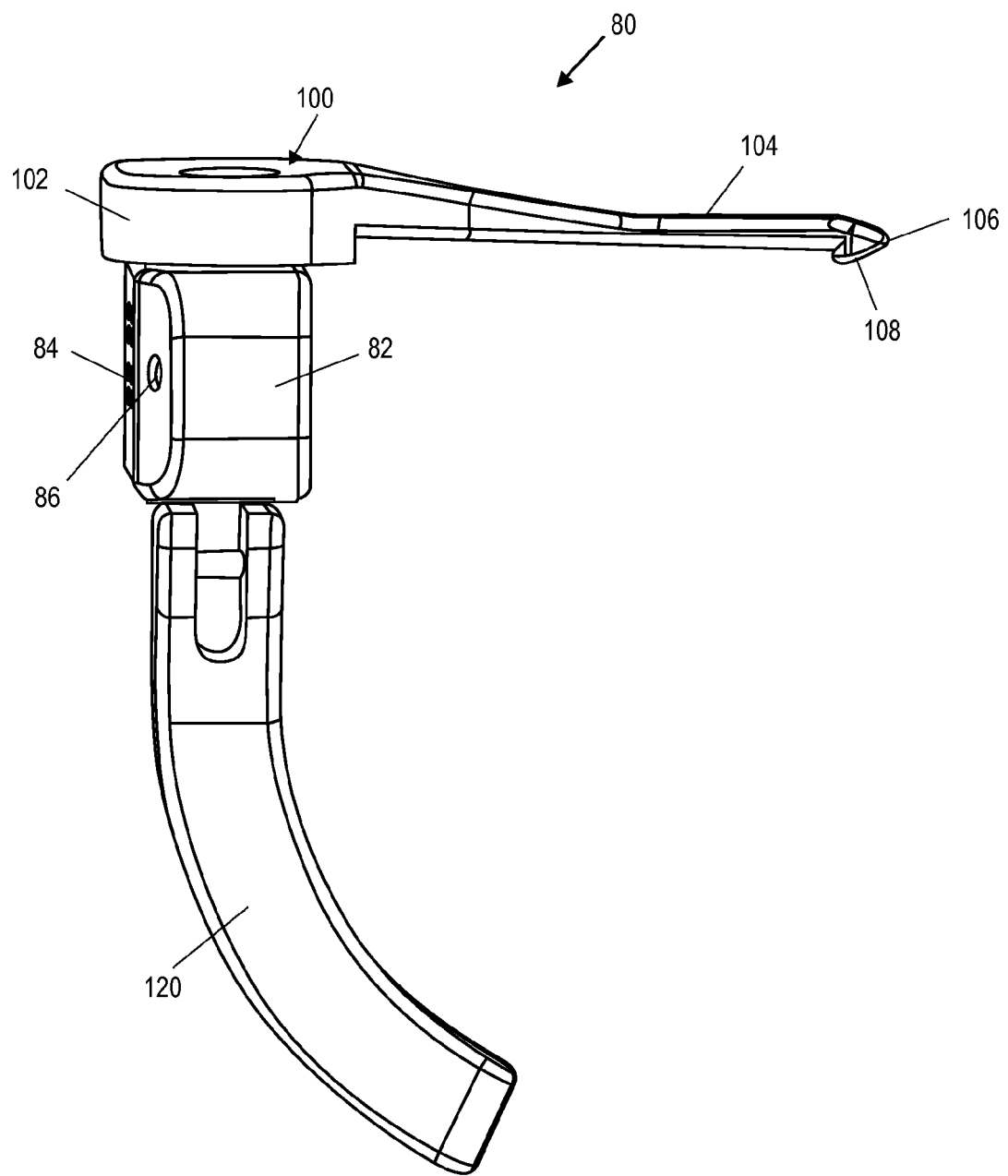
FIG. 4B illustrates a side view of the positioning instrument of FIG. 4A.
Figure 4C:
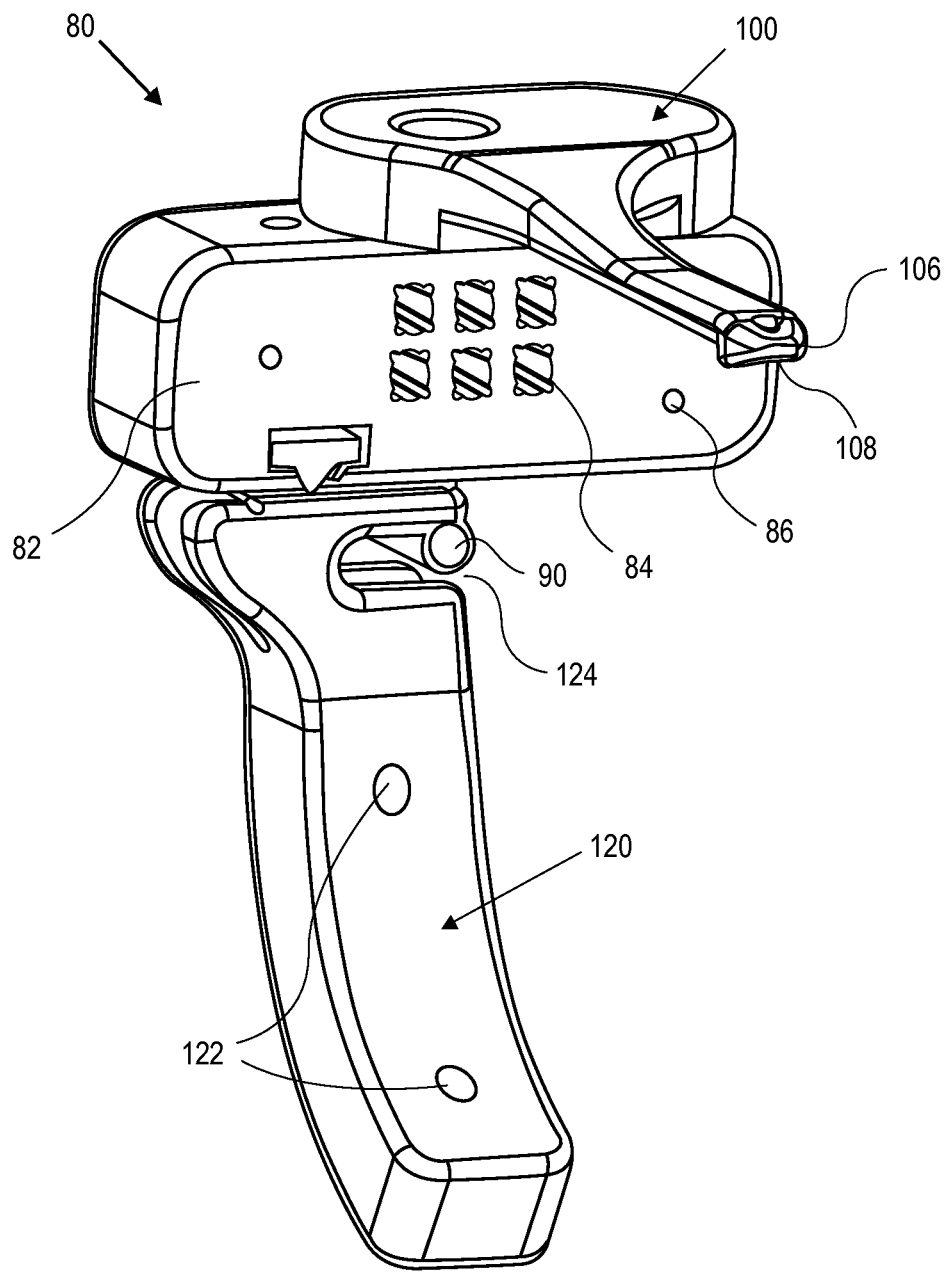
FIG. 4C illustrates a rear view of the positioning instrument of FIG. 4A.

As shown and described, the positioning instrument 60 may be provided as a unitary body. However, in some cases, it may be desirable to provide a less obtrusive instrument in the surgical work area. FIGS. 4A-4C illustrate an exemplary embodiment of a modular positioning instrument 80 having detachable components so that less visual space is obstructed during surgery. Furthermore, in some cases not all the components are necessary or desired.

Like positioning instrument 60, modular positioning instrument 80 may include an alignment guide 82 that serves as a jig, or a box/frame for guiding a device to a specific location on the bone being treated. One or more device portals 84 may be provided on the alignment guide 82. Additionally, the alignment guide 82 may include one or more tool receiving openings 86 that allow a tool to be passed through. The tool may be, for example, a pin, needle or drill bit. In one instance, the tool may be a pin to secure the alignment guide 82 to bone, as will be shown and described below.

Figure 5:
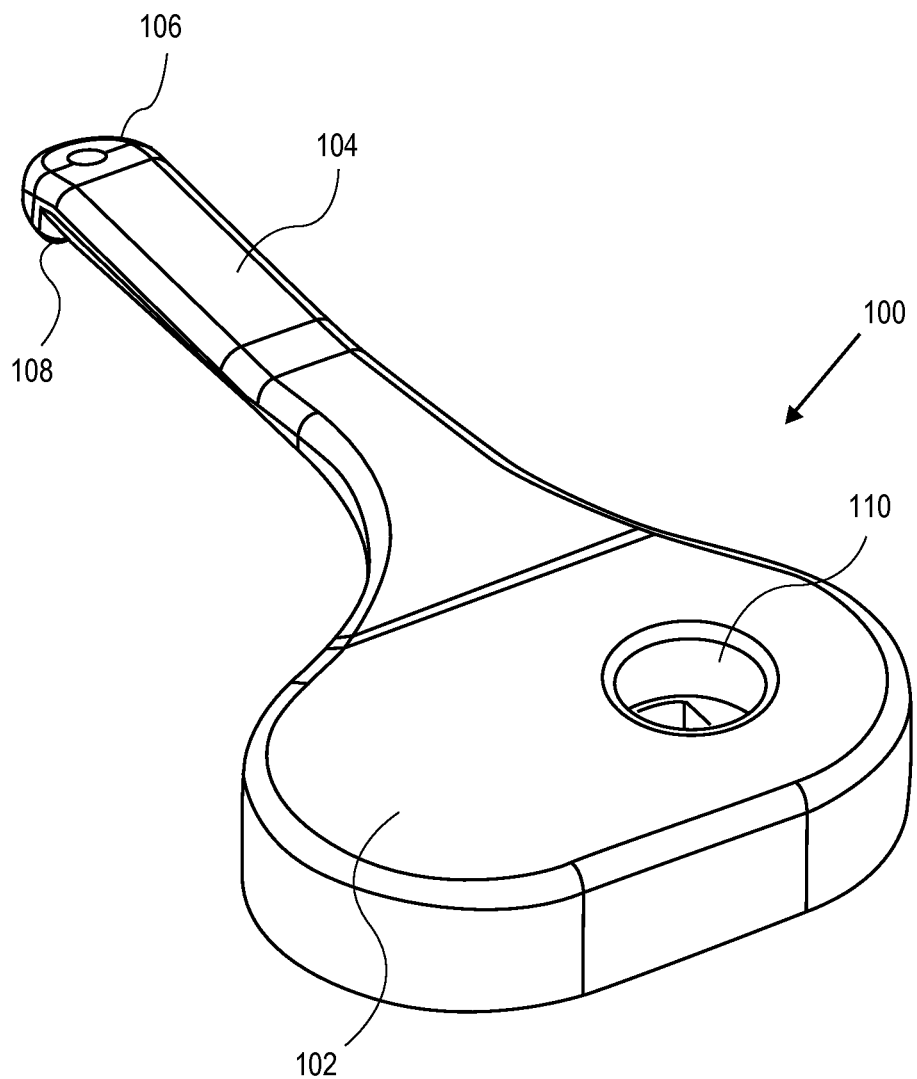
FIG. 5 illustrates a perspective view of an indicator probe of FIG. 4A.

The positioning instrument 80 can also include an optional, detachable indicator probe 100, shown in FIG. 5, for visually identifying the target site. The target site may first be identified arthroscopically, in one example. The indicator probe 100 can include a body 102 from which extends an arm 104 that terminates at a terminal end 106 with a protrusion or knob 108 for visually identifying the target site. It is envisioned that the probe 100 or knob 108 could be configured in any number of designs, so long as they are suited to reach the bone from outside the incision site and identify defects, such as for example single point or multiple point protrusion, or the probe 100 and/or knob 108 could even be configured similar to a guidewire. Additionally, the terminal end 106, indicator probe 100 or any part thereof could include a radiopaque marker for identification during use with x-rays or a C-arm.

Figure 6A:
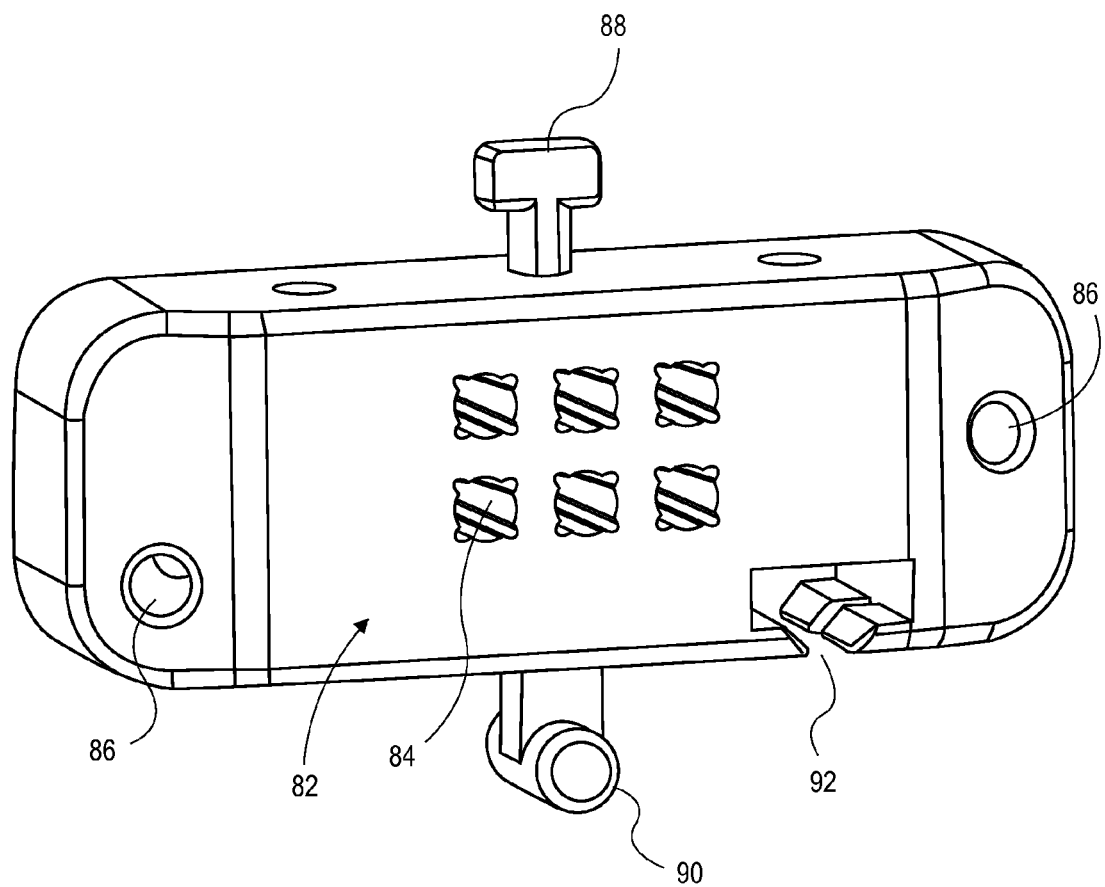
FIG. 6A illustrates a perspective view of an insertion gauge of the positioning instrument of FIG. 4A.
Figure 6B:
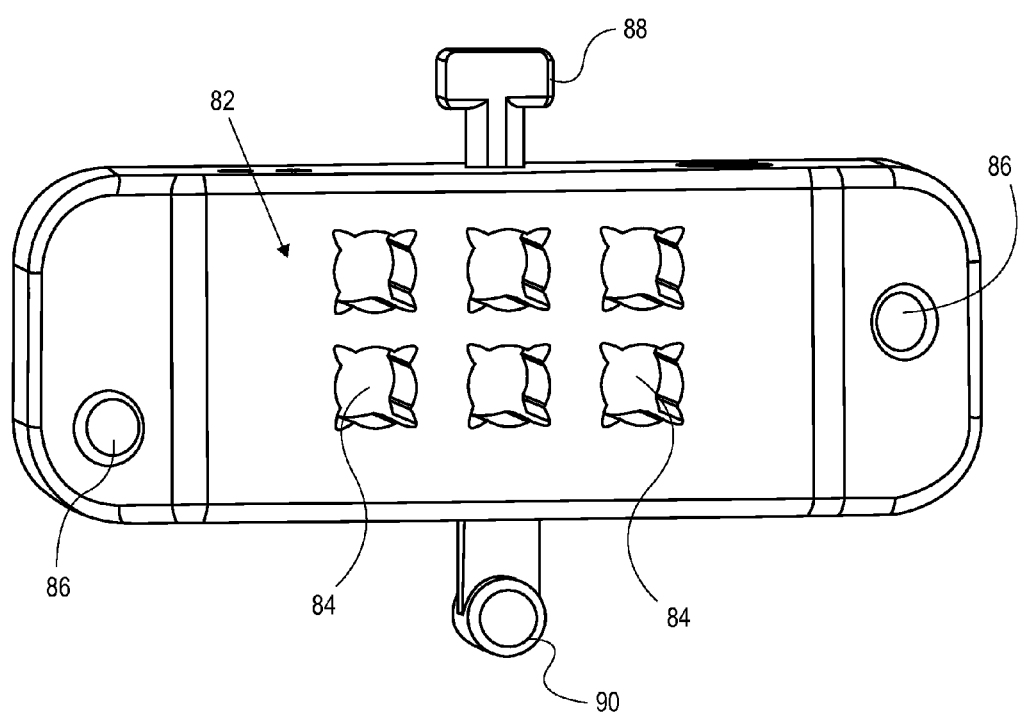
FIG. 6B illustrates a perspective view of another exemplary embodiment of an insertion gauge of the present invention.

The body 102 may further include a bore 110 for receiving a probe-attachment tab 88, as shown in FIGS. 6A and 6B. It is contemplated that any known mechanism for attaching the indicator probe 100 to the probe-attachment tab 88 can be employed, so long as the mechanism allows quick and easy detachment, without disturbing any of the other components of the instrument 80 or tools that may have been employed during its use. For instance, the indicator probe 100 may have a snap-fitted connection to the probe-attachment tab 88. Additionally, indicator probe 100 may be configured to be angularly adjustable relative to the alignment guide 82. A mechanism may be provided to allow the indicator probe 100 to rotate about the alignment guide 82, thereby enabling more flexibility for the clinician to operate the instrument 80.

A detachable inferior guide portion 120 may also optionally be provided with the positioning instrument 80. The inferior guide portion 120 may include one or more tool receiving holes 122 for receiving a tool. The tool may be, for example, a pin, needle or drill bit. In one instance, the tool may be a drill to drill a hole in the bone, as will be shown and described below. Accordingly, the inferior guide portion 120 offers a distal, or inferior approach guide, for targeting the lower area of the target site or other tissue area from different angular approaches through tool-receiving holes 122. In addition, the inferior guide portion 120 can serve as a handle portion of the instrument 80 for manipulating the positioning instrument 80 during use. A notched region 124 of the inferior guide portion 120 may be provided to secure the inferior guide portion 120 to the alignment guide 82. As shown in FIGS. 6A and 6B, the alignment guide 82 may include a handle-attachment tab 90 that is configured to engage the notched region 124 of the inferior guide portion 120. Any known mechanism for attaching the inferior guide portion 120 to the handle-attachment tab 90 can be employed, so long as the mechanism allows quick and easy detachment, without disturbing any other components of the instrument 80 or tools that may have been employed during its use.

As shown in FIGS. 4A-4C and 6A, the alignment guide 82 may include a notched region 92 configured to receive a spring ball detent or mating spring loaded mechanism to create a "snap" fit to hold the alignment guide 82 in place. The notched region 92 is optional, as an embodiment of an alignment guide without the notched region 92 is illustrated in FIG. 6B. Moreover, the notched region 92 may be replaced by a screw, cam lock, or any other mechanism to hold the two components (i.e., the inferior guide portion 120 to the alignment guide 82) together in a simple manner but still allow easy connection and disconnection of the components without disturbing other components of the instrument 80 or other tools that may have been employed during its use.

Figure 7:
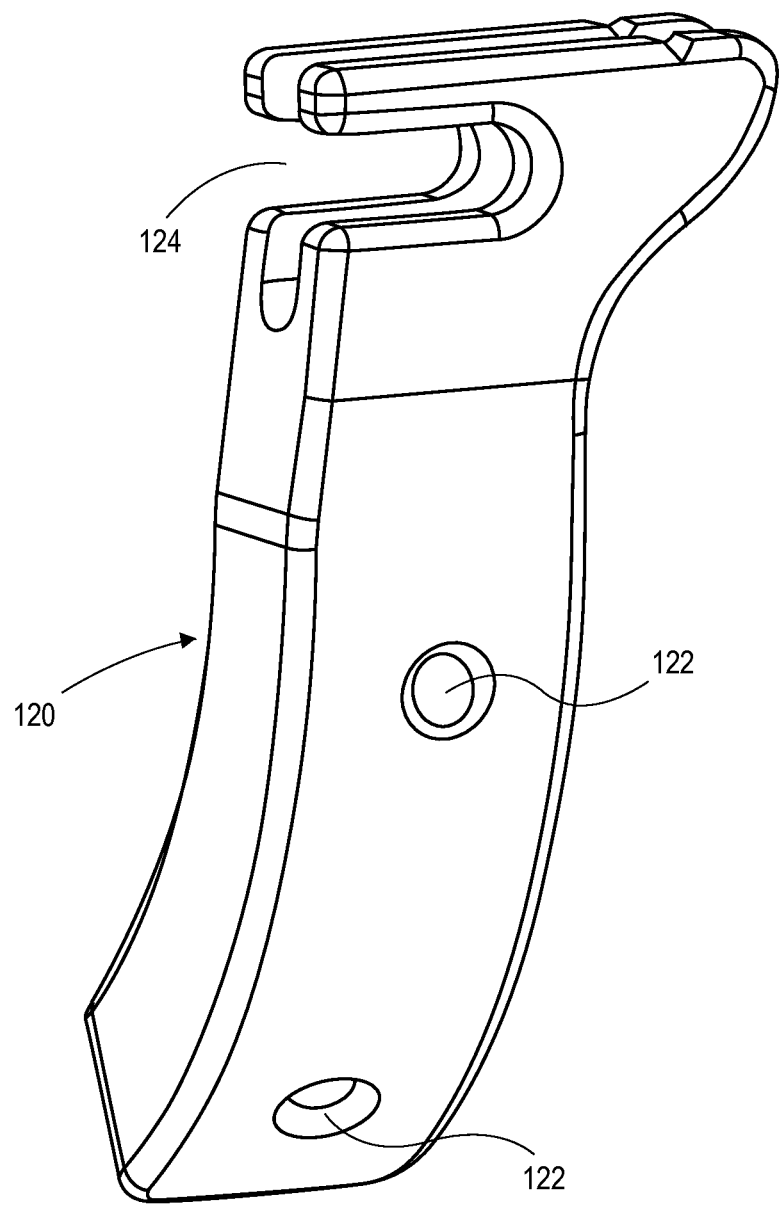
FIG. 7 illustrates a perspective view of the handle of FIG. 4A.
Figure 8:
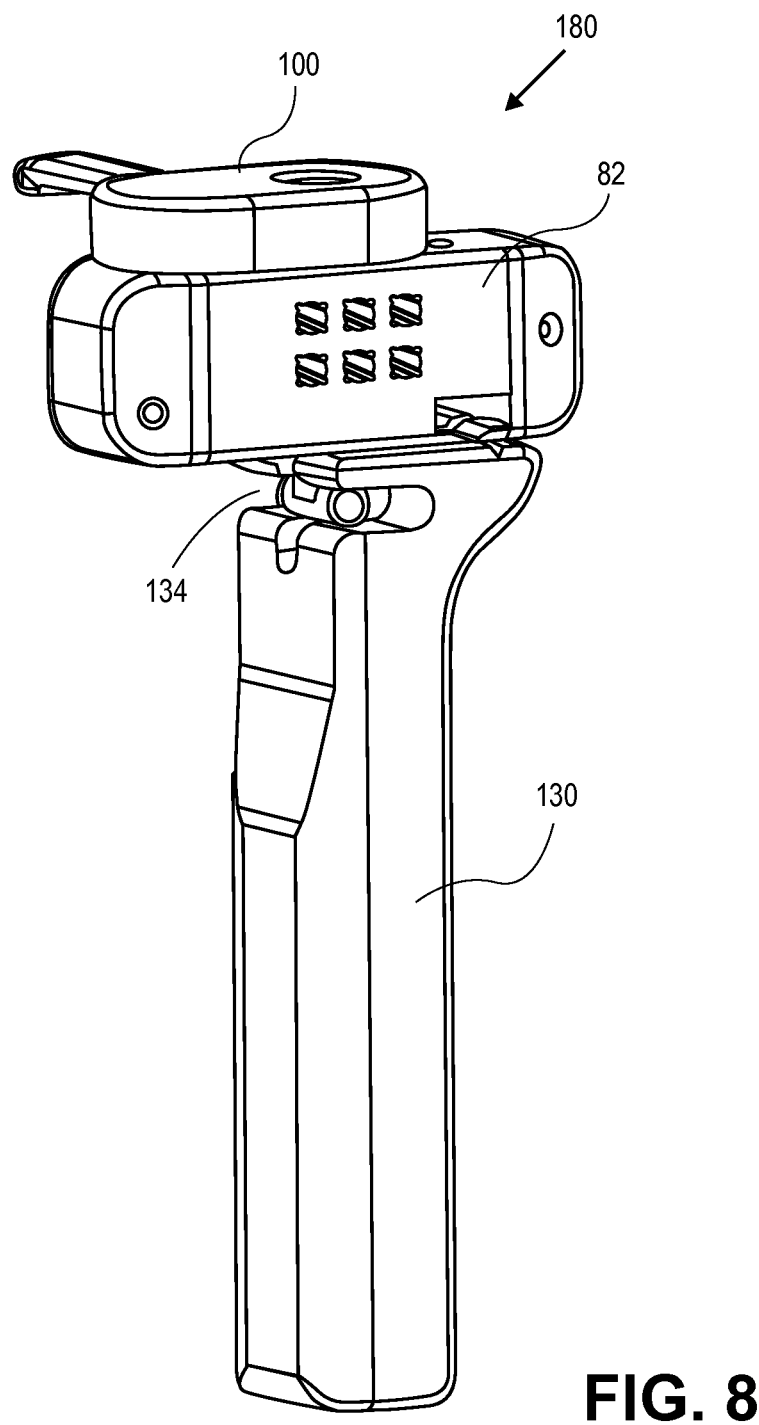
FIG. 8 illustrates a perspective view of another exemplary embodiment of a positioning instrument of the present invention.
Figure 9:
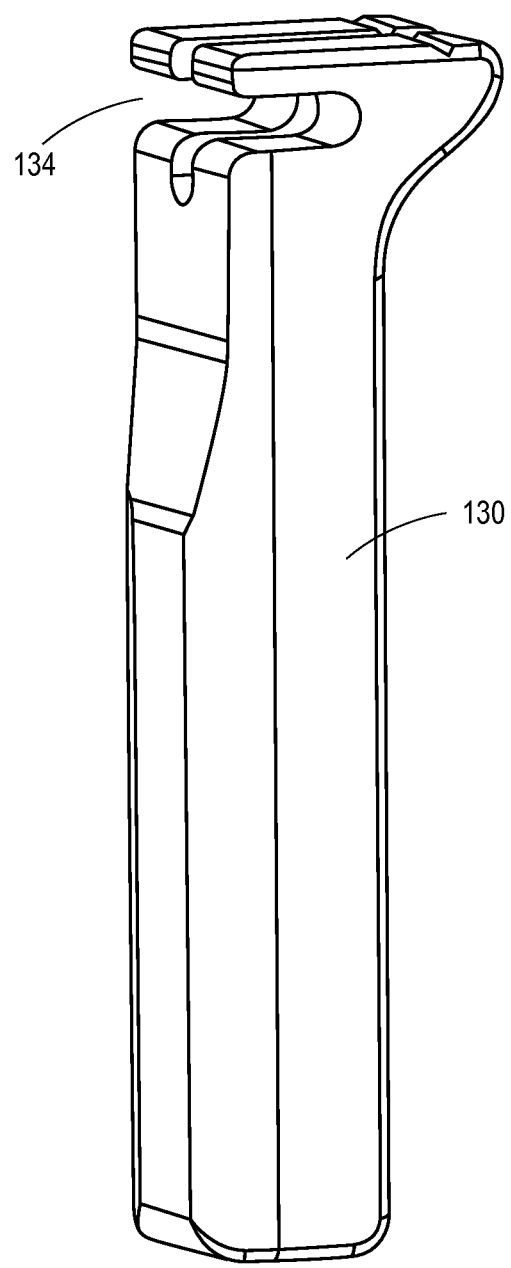
FIG. 9 illustrates a perspective view of the handle of FIG. 8.

FIG. 7 illustrates one exemplary embodiment of the inferior guide portion 120 wherein the main body is curved for easy gripping. FIG. 8 illustrates another exemplary embodiment of a positioning instrument 180 whereby a straight handle portion 130 is attached to the alignment guide 82 and indicator probe 100 previously described. As further shown in FIG. 9, the straight handle portion 130 may include a notched region 134, similar to notched region 124 of curved inferior guide portion 120, for receiving the handle-attachment tab 90 of gauge plate 82. As in the previously described embodiment, any known mechanism for attaching the handle portion 130 to the handle-attachment tab 90 can be employed, so long as the mechanism allows quick and easy detachment, without disturbing any other components of the instrument 180 or tools that may have been employed during its use. In the illustrated embodiment, the straight handle portion 130 does not have tool receiving holes, though it is contemplated that such holes could easily be provided if desired. Moreover, it is possible for the handle portion 130 to be configured for attachment to the operating table for added stability.

Figure 10A:
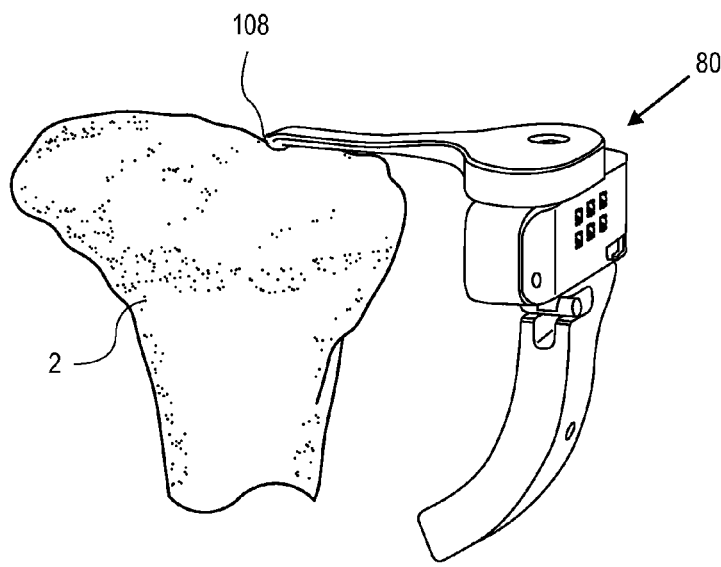
FIGS. 10A-10I illustrate various steps of using the positioning instrument of FIG. 4A.

FIGS. 10A-10I illustrate an exemplary method of using the modular positioning instrument 80 with the insertion tool 40 and implant 30 of the present disclosure to repair a bone defect in a tibia 2 having a bone marrow lesion in the subchondral bone. The method provides a minimally invasive, tissue sparing technique for accessing, identifying and treating the target site. In FIG. 10A, a surgical incision may be made to access the bone to be treated. In the present example, where the bone 2 is a tibia, the target site may be a bone marrow lesion in the subchondral bone. Typically, in these examples, the cartilage above the target site is also damaged, providing a clear visual cue to the clinician of where the defect resides. Alternatively, using MRI or other imaging technology, a clinician may identify a target site for treatment, use a template to mark the site, and extrapolate that template over a C-arm image available in the operating room in a set view. Once identified, either arthroscopically or through imaging technology, the clinician may then target the indicator probe 100 of the modular positioning instrument 80 to the target site, placing the indicator knob 108 of the positioning instrument 80 on top of the tibial bone 2 and over the target site.

Figure 10B:
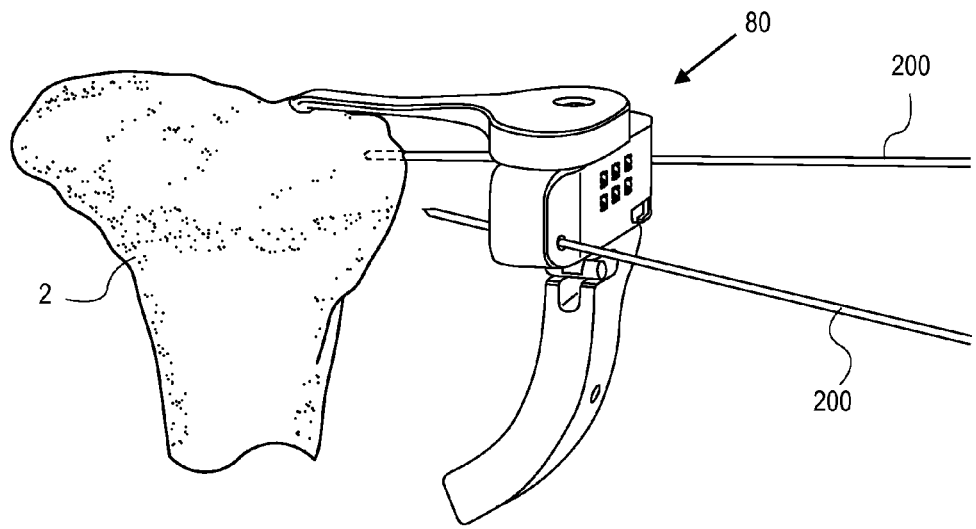

Next, the clinician can secure the positioning instrument 80 in place by inserting superior pins 200 through the tool openings 86 of the alignment guide 82, as illustrated in FIG. 10B. The superior pins 200 may be oriented in a converging or diverging pattern, depending on the clinician's needs. In order to prevent overextension, it is possible to provide the pins 200 with a collar, indicia such as colored bands or measurement marks, or a shoulder section, that would enable the clinician to know how far to insert the pins.

Figure 10C:
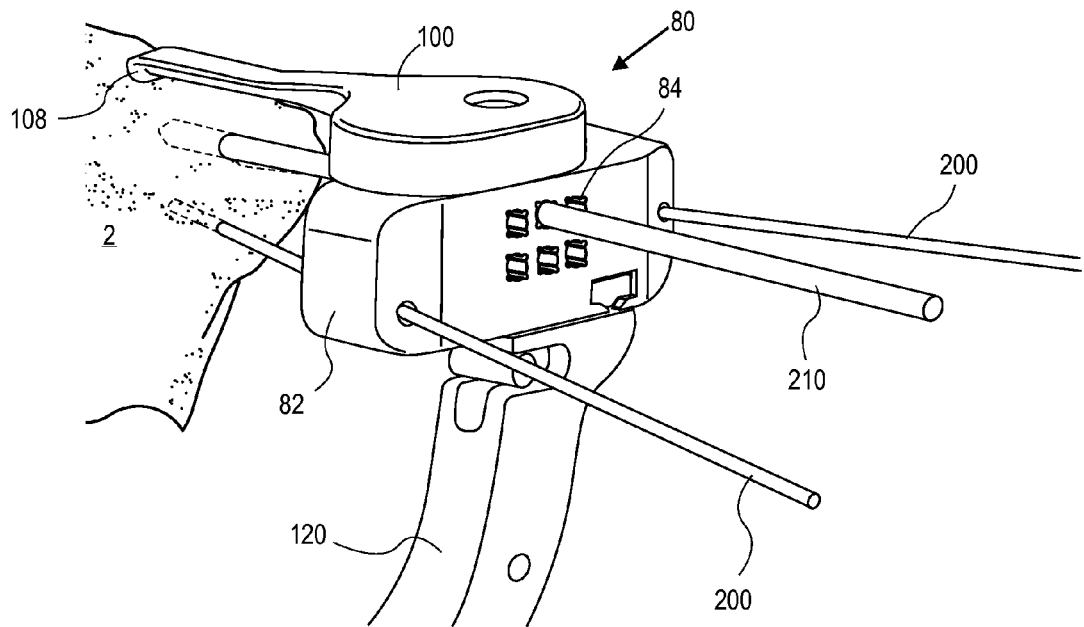
Figure 10D:
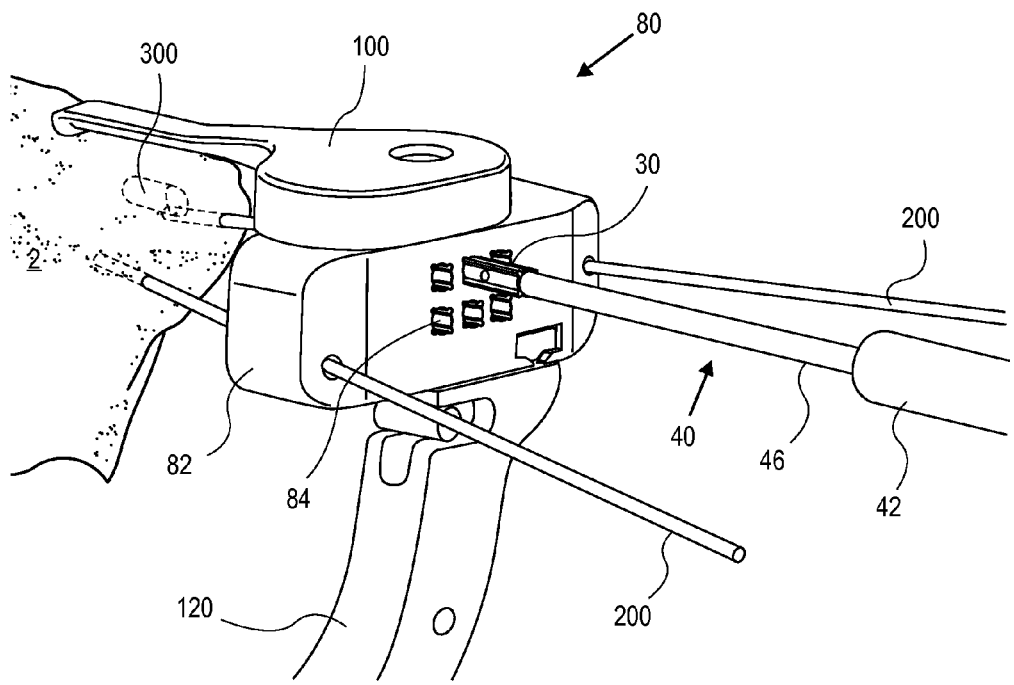
Figure 10E:
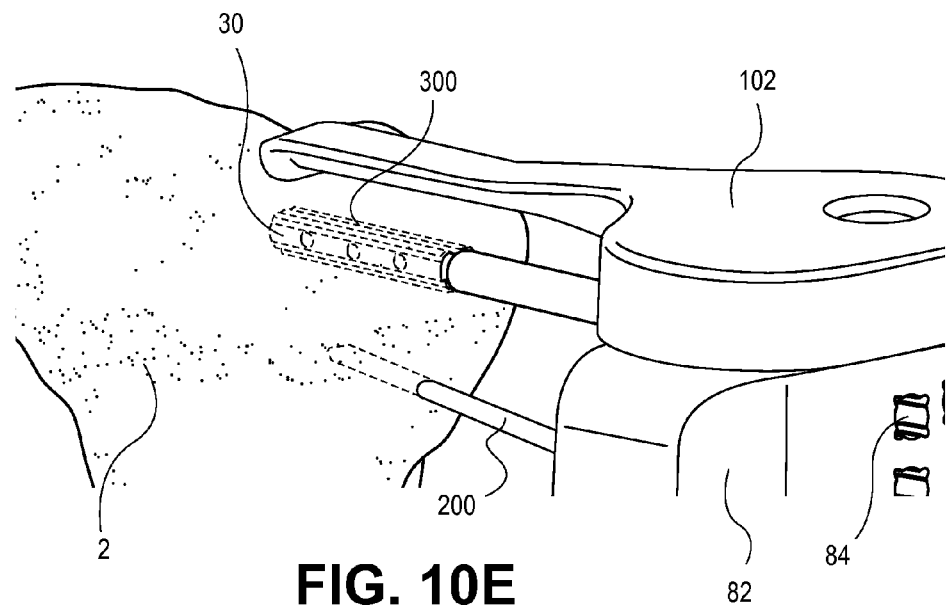

As shown in FIGS. 10C and 10D, once the positioning instrument 80 is stably secured, the clinician may then elect to insert a drill 210 through one of the device portals 84 and drill a hole or cavity 300 proximate to the target site, or bone marrow lesion in this example. After the cavity 300 is created, the drill 210 is removed and then the insertion tool 40 with the implant 30 attached may be placed through the same device portal 84. The implant 30 may be inserted into the cavity 300, as shown in FIG. 10E. As previously mentioned, the positioning instrument 80 is particularly suited to guide, or direct, the implant 30 to be inserted parallel to the top of the bone 2, as illustrated. The cavity 300 may be either larger in diameter than the outer diameter of the implant 30, or it may be nearly the same diameter, depending on whether the clinician desires space around the implant 30 for a biologic material, bone cement or other bone void filler. Where the cavity is nearly the same diameter as the outer diameter of the implant 30, the fins 20 may be configured to allow some space for the biologic material, cement or filler to reside around the implant 30. In other embodiments, the fins 20 may be press-fit into bone to create an interference fit with the cavity 300.

Figure 10F:
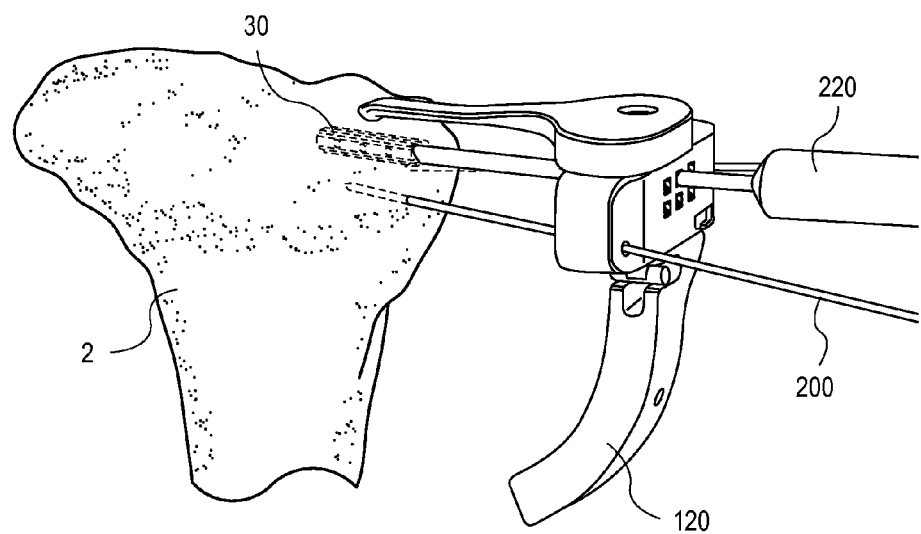

When the implant 30 has been properly inserted, the insertion tool 40 may be removed. If the implant 30 is fenestrated as in the present example, the clinician may elect to inject a bone cement, such as calcium phosphate, for instance, into the implant 30. To accomplish this, an injection catheter 220 filled with bone cement may be placed through the same device portal 84 to the implant 30, as shown in FIG. 10F. The bone cement may then be injected through the implant 30, and the injection catheter 220 removed from the alignment guide 82. In some cases, it may be desirable to provide an implant 30 with a collet (not shown) to prevent overfilling.

Figure 10G:
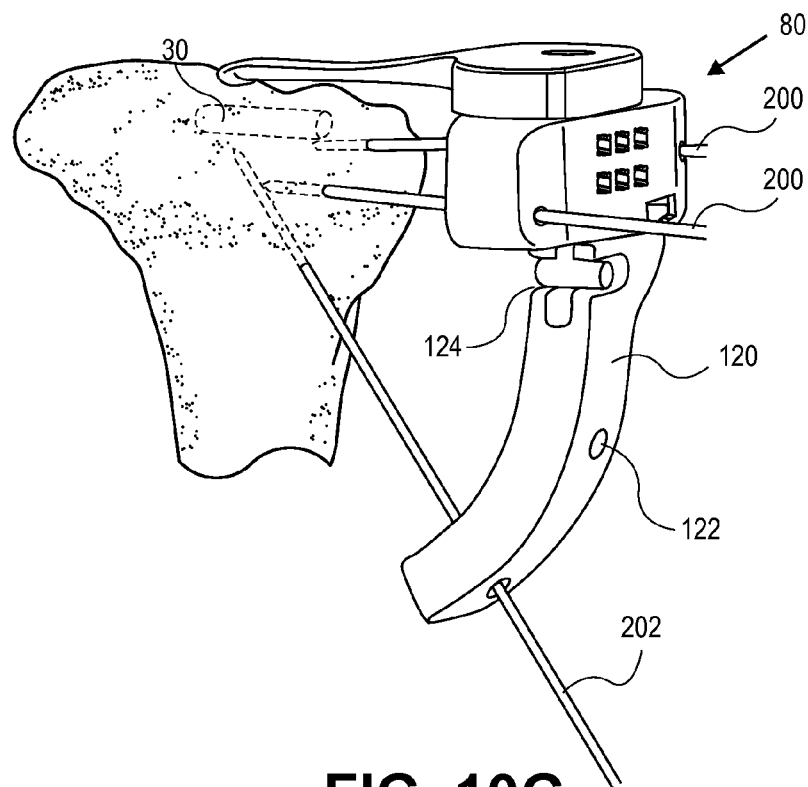
Figure 10H:
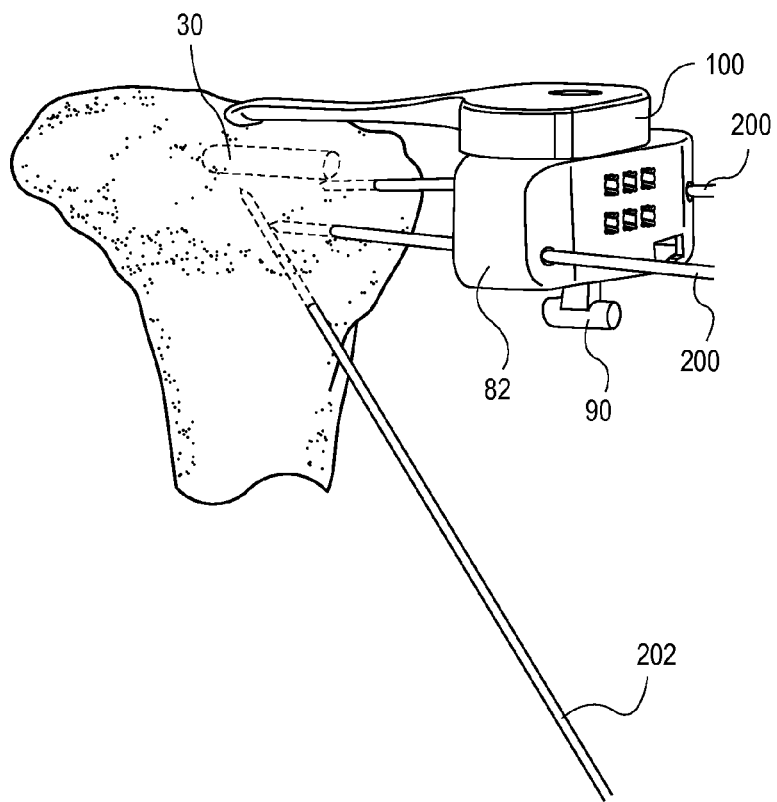

Next, as shown in FIG. 10G, an inferior pin 202 may be placed through one of the tool openings 122 of the inferior guide portion 120. The inferior guide portion 120 may then be removed by undoing the connection between the notched region 124 and the handle-attachment tab 90, and sliding the inferior guide portion 120 down the inferior pin 202. What remains is the alignment guide 82 and the attached indicator probe 100, still secured in place by the pair of pins 200 extending through tool openings 86, as shown in FIG. 10H. If needed, the implant 30 may need to be sealed to prevent cement leakage.

Since the inferior guide portion 120 and the straight handle portion 130 are interchangeable, it is possible to use both components in a step-wise fashion. For instance, it is envisioned that one could first use the straight handle portion 130 to manipulate the positioning instrument 180 in place, then after the alignment guide 82 has been secured with the pins 200, the straight handle portion 130 can be removed and the inferior guide portion 120 attached to allow targeting of tissue inferior to the target site by different angular approaches through tool-receiving holes 122.

Figure 10I:
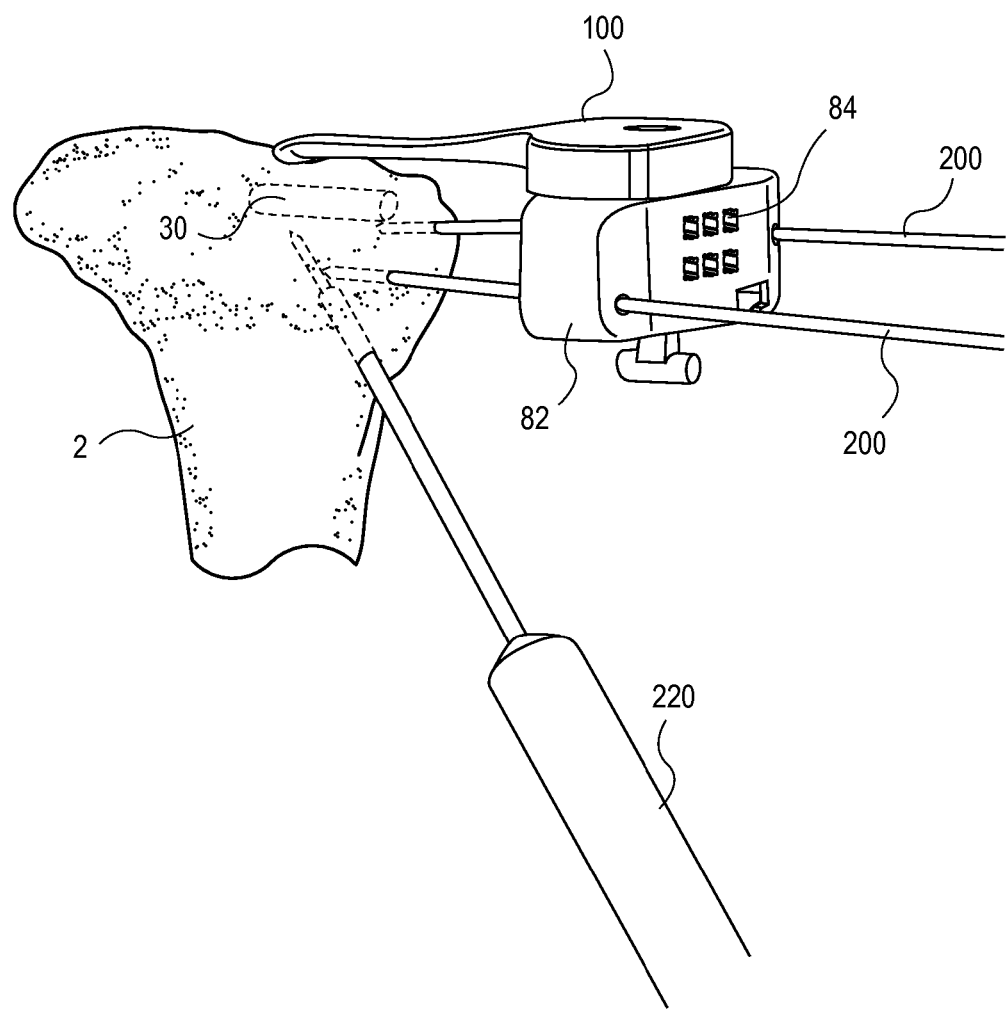
Figure 11A:
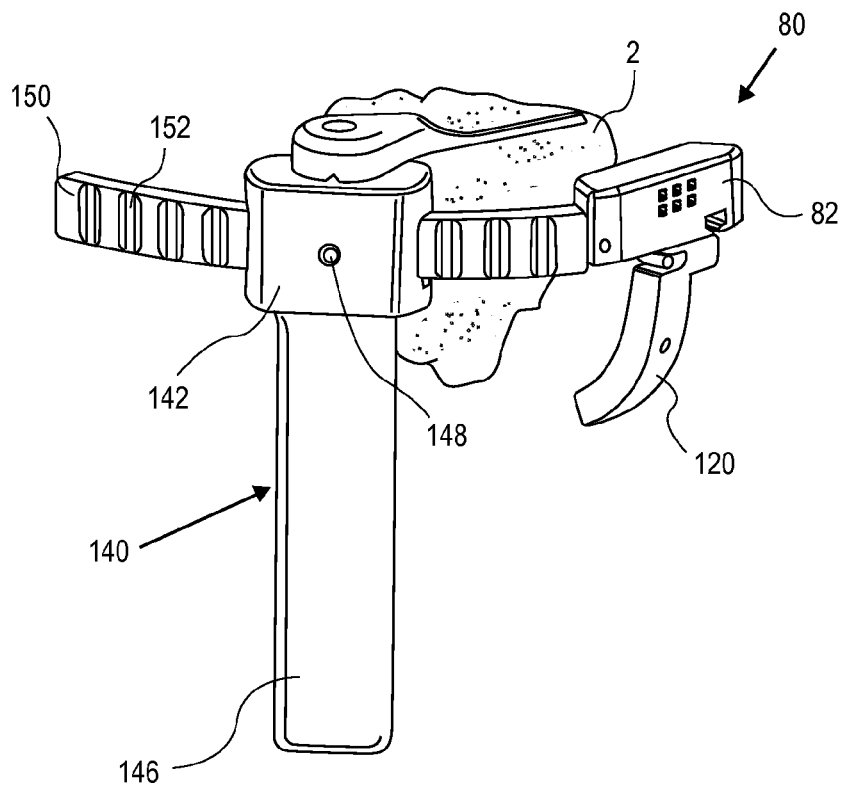
FIG. 11A illustrates a perspective view of yet another embodiment of a positioning instrument of the present invention in situ.
Figure 11B:
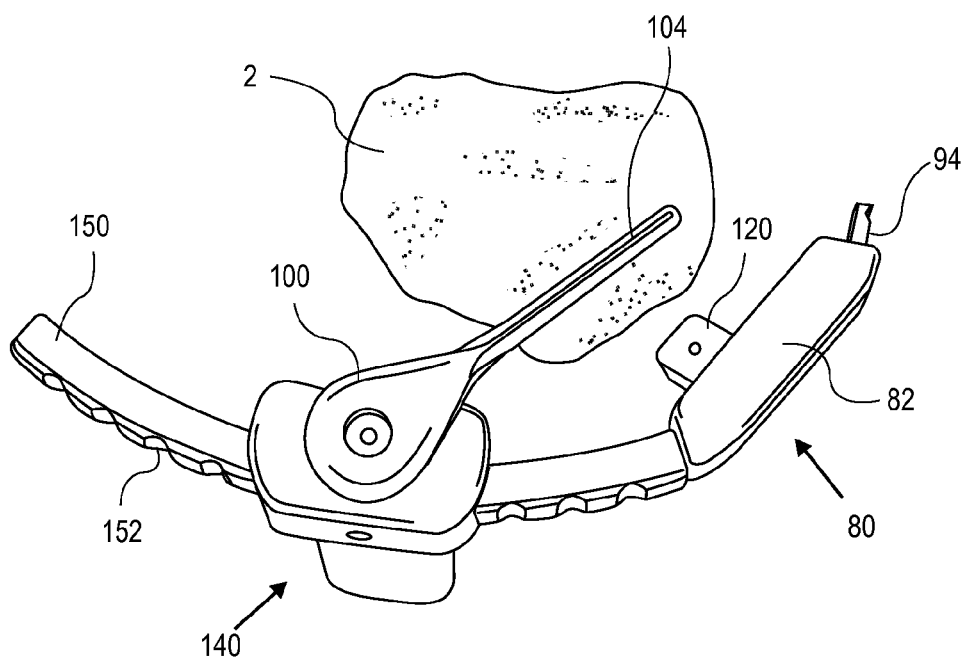
FIG. 11B illustrates a top-down view of the positioning instrument of FIG. 11A in situ.
Figure 11C:
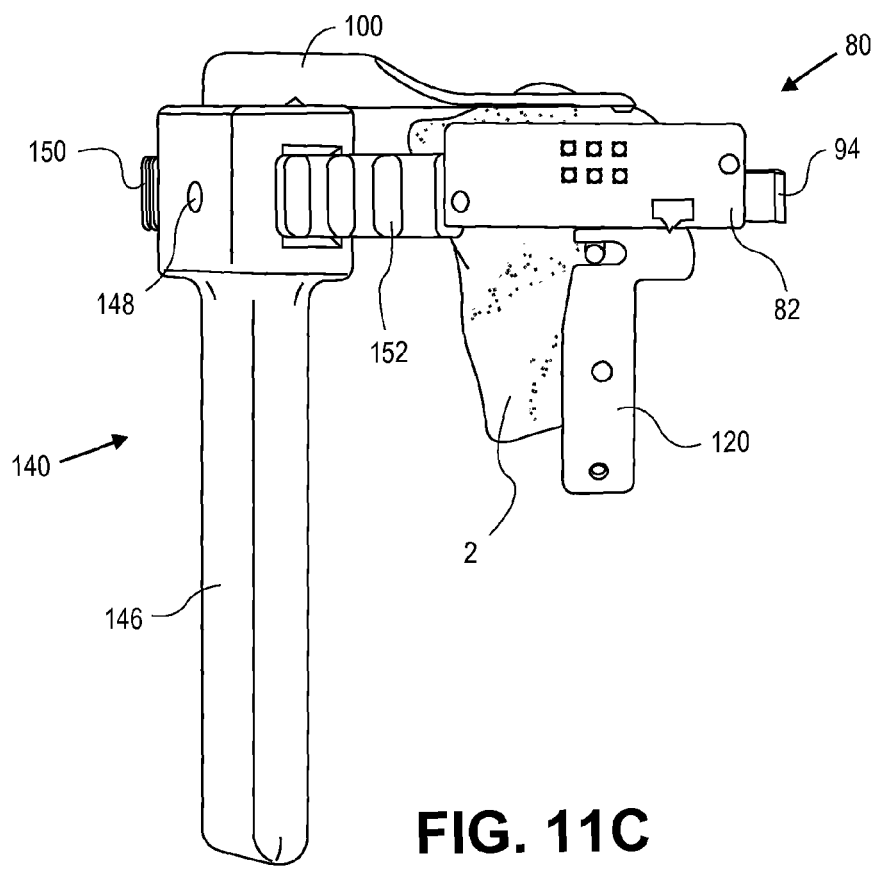
FIG. 11C illustrates a side view of the positioning instrument of FIG. 11A in situ.
Figure 11D:
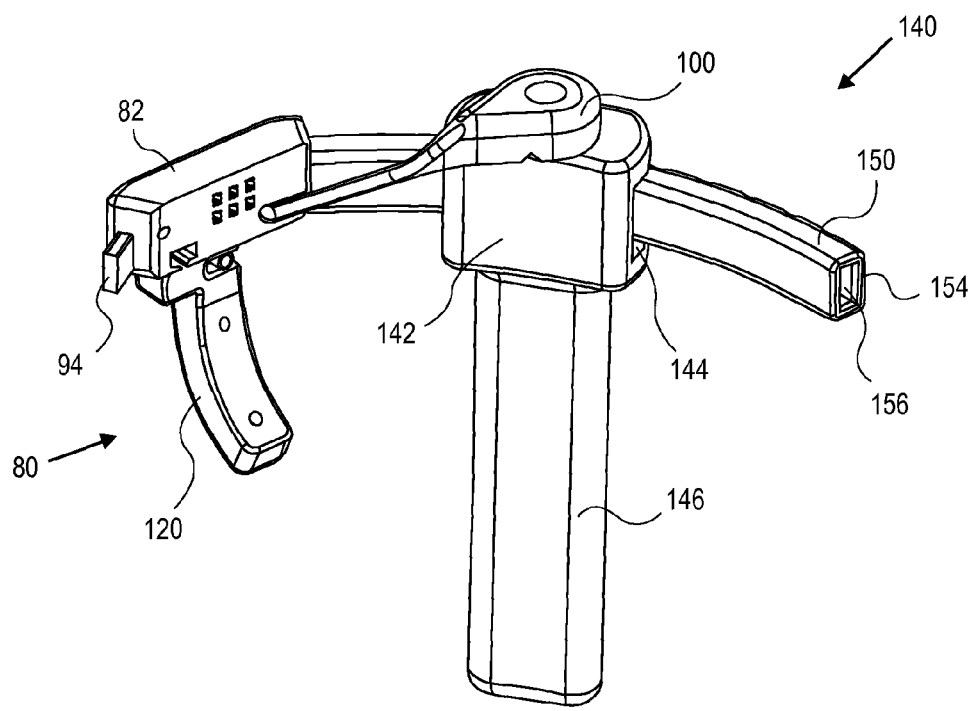
FIG. 11D illustrates a rear view of the positioning instrument of FIG. 11A.

The injection catheter 220 or an injection needle may be slid over the inferior pin 202, and bone cement may be optionally injected below the bone defect, or bone marrow lesion, in this example and as shown in FIG. 10I. Lastly, all instrumentation can be removed and the surgical incision site closed up.

As can be seen in the method just described, the device portals 84 play a crucial role in the clinician's ability to easily and precisely access the target site, particularly when the target site is in a very limited region of the bone such as subchondral bone. The device portals 84 function as spatial references, orientation markers or location markers, and allow the clinician to perform multiple functions in a precise, minimally invasive, tissue sparing manner in less time.

While the method just described and illustrated employs an implant 30 at the target site to treat the bone marrow lesion that is the bone defect in question, it is understood that procedures may be administered using the positioning instrument 80 provided. For instance, any of the specific procedural steps of FIGS. 10A-10I may be performed either alone or in combination in varying order. In one example, the step of cavity creation may be the only function the clinician elects to perform. In another example, the step of cavity creation may be combined with the step of bone cement injection, without the step of inserting an implant into the cavity, though still using the principles of the present disclosure and positioning instrument 80 provided. Moreover, it is possible to use the instruments and implants of the present disclosure to precisely insert more than one implant at the target site, without risk of improper alignment of the implants.

In some cases, it is more desirable to approach the target site at an angle with respect to the entry portal of the indicator probe 100. FIGS. 11A-11D illustrate an exemplary embodiment of a positioning instrument holder 140 that allows for angular orientation of the positioning instrument 80 of the present disclosure. In this example, probe 100 visualization is achieved through a general portal where it is desirable to treat a local area specific to the defect being identified using a percutaneous approach near the defect. As shown, positioning instrument holder 140 may include a central body 142 having a slot 144 for receiving a rail, or track belt, 150. The track belt 150 may be curved and include a plurality of detents 152. The track belt 150 can include a slotted channel 156 extending into each end 154 for receiving side tabs 94 provided on the alignment guide 82. The side tabs 94 may be notched so as to allow the slotted channel 156 to catch, thereby providing an easy catch and release mechanism for securing the alignment guide 82 to the track belt 150. The mechanism can be, for example, a slip fit or an interference fit. If desired, a spring button release may also be employed.

As further illustrated, the central body 142 of the positioning instrument holder 140 may extend into a handle 146, and further include a catch and release mechanism 148, such as a spring button release, for releasable hold of the detents 152 on the track belt 150. The plurality of detents provides incremental angular positioning of the alignment guide 82 relative to the track belt 150. Rather than have the indicator probe 100 adjustably connected to the alignment guide 82, in the present embodiment the indicator probe 100 may be adjustably mounted to the central body 142 of the positioning instrument holder 140. This allows the indicator probe 100 to be indexed to a left or right approach to the target site. However, while the indicator probe 100 is shown to be angularly adjustable relative to the central body 142 in the illustrations, it is understood that the indicator probe may be stationary and rigidly fixed at a right angle relative to the central body if desired.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A surgical positioning instrument for controlled delivery of a device to a target region of a bone, comprising:
   an alignment guide having a plurality of device portals for insertion of a device therethrough and toward the target region of the bone, wherein the device portals have a predetermined spatial relationship relative to each other;
   a rail attachable, in the alternative, to a left side of the alignment guide and a right side of the alignment guide;
   a positioning instrument having a body with a slot extending therethrough, the slot sized and shaped to receive the rail to allow for adjustable angular positioning of the alignment guide relative to the positioning instrument; and
   an indicator probe adjustably coupled to the positioning instrument, the indicator probe serving as a reference to the bone and being configured for placement against an anatomical landmark of the bone without breaching a cartilage surface of the bone;
   wherein each device portal is configured to provide accurate and controlled delivery of the device to the target region indicated by the indicator probe; and
   wherein the target region is a projected location that resides along trajectories defined by the device portals and the target region is spaced apart from the indicator probe, the trajectories of the device portals extending parallel or at an angle relative to the indicator probe.

2. The instrument of claim 1, wherein the target region is a subchondral bone region.

3. The instrument of claim 1, wherein one or more of the device portals includes an anti-rotation feature.

4. The instrument of claim 3, wherein the anti-rotation feature comprises a portal shape configuration that matches a shape configuration of the device being inserted.

5. The instrument of claim 1, wherein the alignment guide further includes a hole for insertion of a tool.

6. The instrument of claim 5, wherein the tool is a pin, needle, or drill.

7. The instrument of claim 1, wherein the indicator probe includes an extended arm and a protrusion at a terminal end of the extended arm.

8. The instrument of claim 1, further comprising a handle configured to extend from the alignment guide.

9. The instrument of claim 8, wherein the handle is detachable from the alignment guide.

10. The instrument of claim 1, further comprising an inferior guide portion configured to extend from the alignment guide.

11. The instrument of claim 10, wherein the inferior guide portion is detachable from the alignment guide.

12. The instrument of claim 10, wherein the inferior guide portion includes a curved gripping section.

13. The instrument of claim 10, wherein the inferior guide portion includes a hole for insertion of a tool.

14. The instrument of claim 13, wherein the tool is a pin, needle, or drill.

15. The instrument of claim 1, wherein the rail includes a plurality of detents.

16. The instrument of claim 15, wherein the plurality of detents provides incremental angular positioning of the alignment guide relative to the positioning instrument.

17. The instrument of claim 1, wherein the device is an implantable device.

18. The instrument of claim 1, wherein the device is an insertion tool, drill, injection needle, or catheter.

19. The instrument of claim 16, wherein the positioning instrument includes a catch mechanism for releasable engagement with the detents on the rail.

20. The instrument of claim 1, wherein the rail is curved.

21. The instrument of claim 20, wherein the indicator probe is angularly adjustable relative to the alignment guide.

22. A surgical positioning instrument for controlled delivery of a device to a target region of a bone, comprising:

an alignment guide having a plurality of device portals for insertion of a device therethrough and toward the target region of the bone, wherein the device portals have a predetermined spatial relationship relative to each other;

a rail attachable, in the alternative, to a left side of the alignment guide and a right side of the alignment guide;

a positioning instrument having a body with a slot extending therethrough, the slot sized and shaped to receive the rail to allow for adjustable angular positioning of the alignment guide relative to the positioning instrument;

an indicator probe adjustably coupled to the positioning instrument to allow the indicator probe to be indexed to a left approach or a right approach to the target site, the indicator probe serving as a reference to the bone and being configured for placement against an anatomical landmark of the bone without breaching a cartilage surface of the bone; and an inferior guide portion releasably coupled to the alignment guide;

wherein each device portal is configured to provide accurate and controlled delivery of the device to the target region indicated by the indicator probe; and wherein the target region is a projected location that resides along trajectories defined by the device portals and the target region is spaced apart from the indicator probe, the trajectories of the device portals extending parallel or at an angle relative to the indicator probe.

\* \* \* \* \*